United States Patent
Sikora et al.

(10) Patent No.: US 11,090,333 B2
(45) Date of Patent: Aug. 17, 2021

(54) IMMUNE STIMULATORY FUNCTION AND ANTI-TUMOR ACTIVITY OF TGF-β PRIMED MYELOID DERIVED SUPPRESSOR CELLS (MDSC)

(71) Applicant: Baylor College of Medicine, Houston, TX (US)

(72) Inventors: Andrew Sikora, Houston, TX (US); Padmini Jayaraman, Houston, TX (US); Falguni Parikh, Houston, TX (US); Robin Parihar, Houston, TX (US)

(73) Assignee: Baylor College of Medicine, Houston, TX (US)

( * ) Notice: Subject to any disclaimer, the term of this patent is extended or adjusted under 35 U.S.C. 154(b) by 250 days.

(21) Appl. No.: 15/759,717

(22) PCT Filed: Sep. 14, 2016

(86) PCT No.: PCT/US2016/051701
§ 371 (c)(1),
(2) Date: Mar. 13, 2018

(87) PCT Pub. No.: WO2017/048822
PCT Pub. Date: Mar. 23, 2017

(65) Prior Publication Data
US 2019/0046569 A1    Feb. 14, 2019

Related U.S. Application Data

(60) Provisional application No. 62/218,246, filed on Sep. 14, 2015.

(51) Int. Cl.
| | |
|---|---|
| *A61K 35/15* | (2015.01) |
| *A61K 35/26* | (2015.01) |
| *A61K 35/28* | (2015.01) |
| *C12N 5/0789* | (2010.01) |
| *A61P 35/00* | (2006.01) |
| *A61K 35/12* | (2015.01) |
| *A61K 39/00* | (2006.01) |
| *A61K 45/06* | (2006.01) |

(52) U.S. Cl.
CPC .............. *A61K 35/15* (2013.01); *A61K 35/26* (2013.01); *A61K 35/28* (2013.01); *A61P 35/00* (2018.01); *C12N 5/0647* (2013.01); *A61K 39/00* (2013.01); *A61K 45/06* (2013.01); *A61K 2035/124* (2013.01); *C12N 2501/15* (2013.01)

(58) Field of Classification Search
CPC .. A61K 35/15; A61K 35/28; A61K 2035/124; C12N 5/0647; C12N 2501/15; A61P 35/00
See application file for complete search history.

(56) References Cited

U.S. PATENT DOCUMENTS

| | | |
|---|---|---|
| 2014/0086869 A1 | 3/2014 | Chen |
| 2015/0174203 A1 | 6/2015 | Chen et al. |

FOREIGN PATENT DOCUMENTS

WO    2013/169386 A1    11/2013

OTHER PUBLICATIONS

Lechner et al., Characterization of cytokine-induced myeloid-derived suppressor cells from normal human peripheral blood mononuclear cells. Journal of Immunology, vol. 185, No. 4 (Aug. 15, 2010) pp. 2273-2284. (Year: 2010).*
Jayaraman et al., TGF-β1 programmed myeloid-derived suppressor cells (MDSC) acquire immune-stimulating and tumor killing activity capable or rejecting established tumors in combination with radiotherapy. OncoImmunology, vol. 7, No. 10 (2018) pages (Year: 2018).*
Lechner et al., Myeloid-derived suppressor cell induction and mechanisms of suppression in 100 human solid tumor cell lines. Molecularand Cellular Biology and Immune Escape in Cancer, (Feb. 7-12, 2010). Silverthorne, CO. Keystone Symposia on Molecular and Cellular Biology. p. 182. (Year: 2.*
Youn et al., The biology of myeloid-derived suppressor cells: The blessing and the curse of morphological and functional heterogeneity. European Journal of Immunology, vol. 40, No. 11 (Nov. 2010) pp. 2969-2975. (Year: 2010).*
Shvedova et al. "MDSC and TGF-β are required for facilitation of tumor growth in the lungs of mice exposed to carbon nanotubes", Cancer res, Apr. 15, 2015, vol. 75, No. 8, pp. 1615-1623.
Lu et al. "Myeloid cell-derived inductible nitric oxide synthase suppresses M1 macrophage polarization", Nature Communications, Mar. 25, 2015, vol. 6, No. 6676, pp. 1-14.

* cited by examiner

Primary Examiner — Kara D Johnson
(74) Attorney, Agent, or Firm — Norton Rose Fulbright US LLP

(57) ABSTRACT

Embodiments of the disclosure concern methods and compositions related to cancer therapy using myeloid derived suppressor cells (MDSC) as a solo therapy or an adjunct therapy. The MDSCs are prepared by exposing bone marrow cells or blood cells to one or more compositions that induce their differentiation to MDSCs and also to TGF-β1, and in specific embodiments the exposure to TGF-β1 results in the MDSCs having anti-tumor activity and/or immune stimulatory activity.

23 Claims, 20 Drawing Sheets

Note: Same method as above except SCC47 tumor sup was used instead of cytokines

IMMUNE STIMULATORY FUNCTION AND ANTI-TUMOR ACTIVITY OF TGF-β PRIMED MYELOID DERIVED SUPPRESSOR CELLS (MDSC)

This application is a national phase application under 35 U.S.C. § 371 that claims priority to International Application No. PCT/US2016/051701 filed Sep. 14, 2016, which claims priority to U.S. Provisional Patent Application Ser. No. 62/218,246, filed Sep. 14, 2015, all of which are incorporated by reference herein in their entirety.

STATEMENT REGARDING FEDERALLY SPONSORED RESEARCH OR DEVELOPMENT

This invention was made with government support under 5K08CA154963-05 awarded by National Cancer Institute. The government has certain rights in the invention.

TECHNICAL FIELD

The technical field of the disclosure includes at least the fields of cell biology, molecular biology, immunology, and medicine, including cancer medicine.

BACKGROUND OF THE INVENTION

Myeloid derived suppressor cells (MDSC) are a heterogeneous population of myeloid progenitors and immature cells that arise from the bone marrow. Cancer-associated inflammatory signals induce MDSC and maintain them in an undifferentiated, immunosuppressive state. MDSCs inhibit T cell proliferation and activation via multiple mechanisms, including upregulation of inducible nitric oxide synthase (iNOS)), arginase (ARG), programmed death ligand 1 (PD-L1), and reactive oxygen species (ROS), thereby suppressing anti-tumor immunity.

The present disclosure provides a solution to the long-felt need in the art for reversal of suppression of anti-tumor immunity by MDSC.

BRIEF SUMMARY OF THE INVENTION

Embodiments of the disclosure concern methods and/or compositions suitable for treating cancer. In specific embodiments, the methods and/or compositions encompass an immunotherapeutic approach that may be utilized for a sole therapy for cancer or in conjunction with one or more other cancer therapies. The individual may have any kind of cancer, whether or not it is solid tumor.

In particular embodiments, immune cells are employed that under normal circumstances and conditions would be contraindicated for cancer therapy. In specific embodiments, immune cells that normally would not be useful for cancer therapy are subjected to one or more events and/or to one or more conditions and/or to one or more compositions that allow the cells to change at least one of their activities such that they are useful for cancer therapy. In specific embodiments, progenitor cells that upon development differentiate into certain immune cells are exposed to one or more factors to alter at least one of their normal functions such that they become useful for cancer therapy.

In particular embodiments, blood cells, bone marrow cells, or a mixture thereof are subjected to one or more events and/or to one or more conditions and/or to one or more compositions such that they differentiate into MDSC but also are exposed to one or more events and/or to one or more conditions and/or to one or more compositions such that they are useful for cancer therapy. In specific embodiments following exposure to one or more events and/or to one or more conditions and/or to one or more compositions, the MDSC lose capacity to suppress T cell proliferation and obtain anti-tumor activity and/or immune stimulatory activity (including at least increasing proliferation of other immune cells, such as T cells, for example). In particular embodiments, blood cells, bone marrow cells, or a mixture thereof are exposed to an effective amount of one or more compositions that allow them to differentiate into MDSC but are also exposed to an effective amount of one or more compositions that allow the MDSC to exhibit anti-tumor activity and/or immune stimulatory activity. In specific embodiments, the exposure of the blood cells, bone marrow cells, or a mixture thereof to an effective amount of transforming growth factor beta 1 (TGF-β1) allows the ultimate MDSC to exhibit anti-tumor activity and/or immune stimulatory activity, when in the absence of the TGF-β1 the MDSC would not exhibit anti-tumor activity and/or immune stimulatory activity.

In embodiments of the disclosure, TGF-β1 alters the function of MDSC, making them anti-tumorigenic. The present disclosure allows elucidation of the effect of TGF-β1 on MDSC generation and function. In specific embodiments, the effect of TGF-β1-conditioned MDSC on tumor growth is characterized.

In an embodiment, there is an isolated plurality of MDSC comprising anti-tumor activity and/or immune stimulatory activity. In a specific embodiment, the MDSCs comprise anti-tumor activity and/or immune stimulatory activity following one or more exposures to an effective amount of TGF-β1. In particular embodiments, the plurality is suspended in a pharmaceutically acceptable carrier or a culture.

In one embodiment, there is a method of generating the plurality of cells of the disclosure, comprising the steps of providing or obtaining mammalian bone marrow cells or blood cells; exposing the bone marrow cells or blood cells to an effective amount of TGF-β1; exposing the bone marrow cells or blood cells to an effective amount of one or more compositions that induce differentiation of the bone marrow cells or blood cells to MDSCs, wherein the steps occur under suitable conditions to produce the plurality of MDSC comprising anti-tumor activity and/or immune stimulatory activity. In some cases, either of the two exposing steps is optional. In a specific embodiment, the exposing steps occur ex vivo. In a particular embodiment, the exposing steps occur at substantially the same time or at different times; the exposing steps may occur at overlapping times.

In a specific embodiment, the one or more compositions that induce differentiation of the bone marrow cells or blood cells comprises supernatant from cancer cells. In certain aspects, the supernatant from cancer cells is obtained from cancer cells engineered to overexpress TGF-β1. The supernatant may come from cancer cells from a cancer patient (as in an autogenous patient-derived tumor), or it may come from cell lines. The supernatant is not patient-specific or cancer type-specific. In specific embodiments, the one or more compositions that induce differentiation of the bone marrow cells or blood cells comprises one or more cytokines, such as cytokines selected from the group consisting of IL-6, VEGF, IL-1, GM-CSF, M-CSF, TNF-α, Prostaglandin E2, and a combination thereof. In some cases, the cytokines are obtained from the supernatant of cells.

In certain embodiments, the effective amount of TGF-β1 utilized in methods of the disclosure is 1 ng/ml through 10 ng/ml. In specific embodiments, the duration of the exposing steps occurs over the course of minutes, hours, days, weeks, or months. In some aspects, the duration of the exposing steps occurs over the course of days, such as from 3-10 days.

In certain embodiments of methods of the disclosure, the bone marrow cells or blood cells are exposed to soluble inflammation-associated signaling mediators, such as that selected from the group consisting of PGE2, ATP, adenosine, agonists of toll-like receptors, other receptors driving innate immunity, and a combination thereof.

In particular aspects, BM progenitor cells exposed to tumor supernatants are the cells that produces MDSC with anti-tumor activity and/or immune stimulatory activity. In specific aspects, addition of TGF-β1 exogenously to blood PBMC in the presence of GM-CSF and IL-6 produces MDSC with anti-tumor activity and/or immune stimulatory activity. In other specific aspects, addition of TGF-β1 exogenously to PBMC in the presence of tumor supernatants produces MDSC with anti-tumor activity and/or immune stimulatory activity.

In particular embodiments, a plurality of cells of the disclosure are provided to an individual. In some cases, the bone marrow or blood cells are obtained from the individual. In particular embodiments, the individual has cancer. A portion of the plurality of MDSCs may be tested for one or more markers, for example, markers selected from the group consisting of iNOS, NO, ROS, ARG, PD-1, PD-L1, transcription factor CREB, and a cell surface marker (such as a cell surface marker selected from the group consisting of CD11b, CD33, MHC II, GR-1, CD14, and a combination thereof). In specific embodiments, a portion of the plurality of MDSC cells are tested for anti-proliferation activity.

In one embodiment, there is a method of treating an individual for cancer, comprising the step of providing an effective amount of MDSC cells to the individual, wherein the induction of the MDSC cells occurred in the presence of an effective amount of TGF-β1. In a specific embodiment, the induction of the MDSC cells occurred according to any method encompassed by the disclosure. In some embodiments, the individual is provided an additional therapy, such as one that comprises immunotherapy, chemotherapy, hormone therapy, gene therapy, surgery, radiation therapy, therapy with small molecule inhibitors, or molecular targeted therapy.

In one embodiment, one may convert in situ MDSC or MDSC precursor cells to TGFβ primed MDSC with TGFβ1 directed preferentially to the MDSC. In specific cases, this may take the form of targeting TGFβ to myeloid precursor cells existing in situ in hematopoietic, lymphoid, tumor, or other tissues of the body, with the end result of such targeting being the in situ production of TGFβ-primed MDSC. Cell type specific targeting could be accomplished by a variety of means familiar to those skilled in the art, including delivery via nanoparticles, liposomes, antibody conjugates, aptamer conjugates, and other methods commonly utilized to direct a drug to a specific cell type.

In a related embodiment, MDSC already existing in the hematopoietic, lymphoid, tumor or other tissues of the body are treated with TGFβ, with the end result of generating TGFβ-primed MDSC with functional properties consistent with TGFβ-primed MDSC generated from myeloid precursor cells. In this embodiment, TGFβ treatment may take the form of cellular targeting of existing MDSC in situ, as described above; or accomplished by harvesting MDSC from peripheral blood, bone marrow, lymphoid, or tumor tissue, and exposing the MDSC to TGFβ ex vivo, for example.

Other and further objects, features, and advantages would be apparent and eventually more readily understood by reading the following specification and by reference to the accompanying drawings forming a part thereof, or any examples of the presently preferred embodiments of the invention given for the purpose of the disclosure.

BRIEF DESCRIPTION OF THE DRAWINGS

For a more complete understanding of the present invention, reference is now made to the following descriptions taken in conjunction with the accompanying drawing, in which.

DETAILED DESCRIPTION OF THE INVENTION

Figure 1:
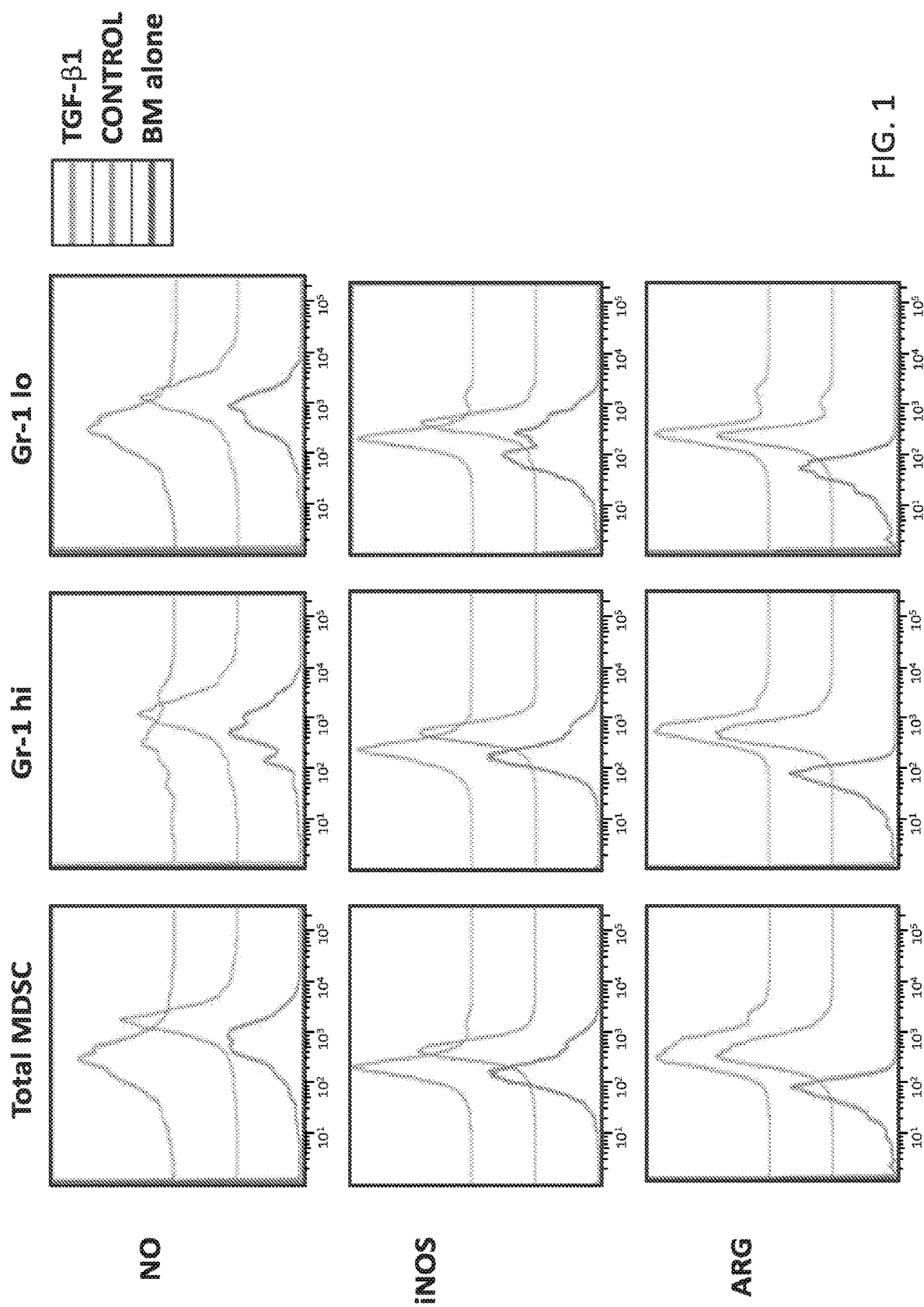
FIG. 1 demonstrates cellular surface marker profile of control vs. TGF-β1 primed MDSCs that were derived with MT-RET melanoma tumor supernatants. (NO—nitric oxide, iNOS—inducible nitric oxide synthase, ARG—arginase)
Figure 2:
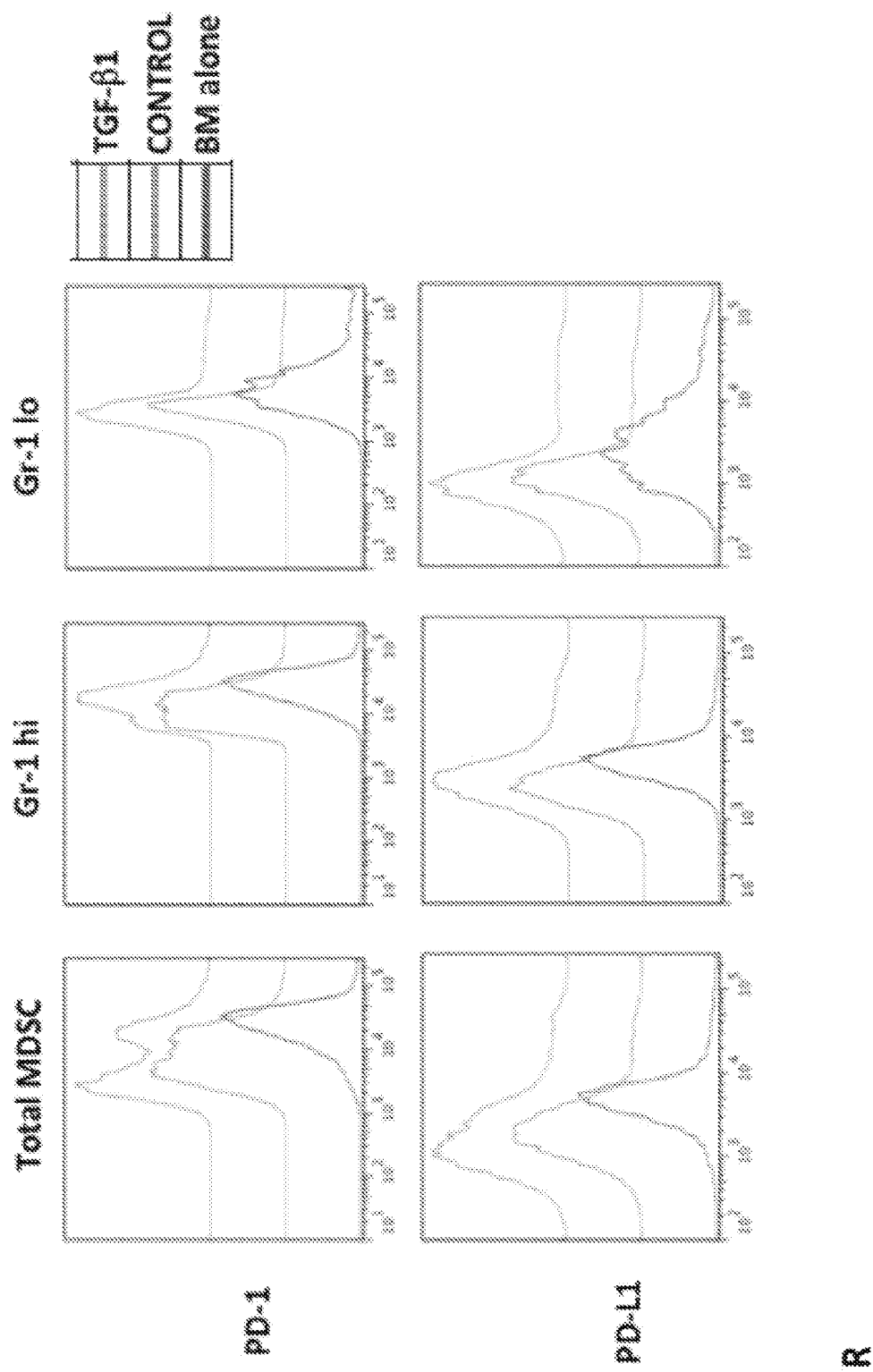
FIG. 2 demonstrates additional cellular profiles for the cells assayed in FIG. 1. (PD-1—programmed death-1, PD-L1—programmed death ligand 1)
Figure 3:
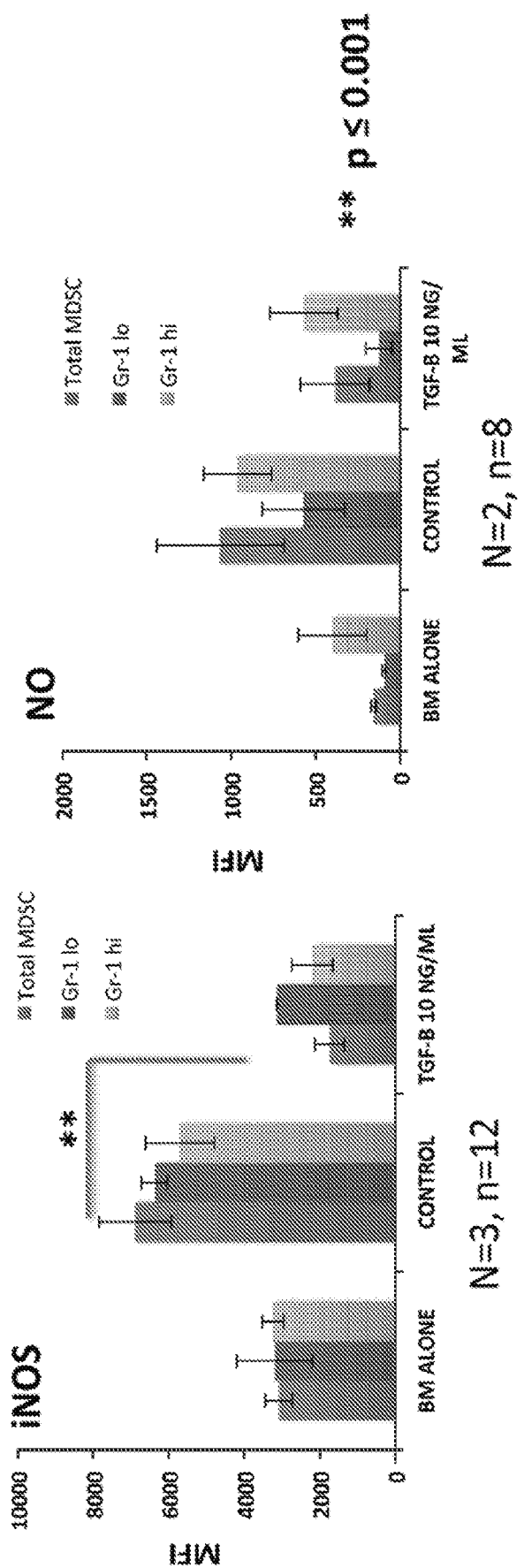
FIG. 3 shows that iNOS/NO expression is decreased in GR-1hi and lo populations from TGFβ-1 primed MDSCs that were derived with MT-RET melanoma tumor supernatants. The data is the summary of 3 and 2 experiments, respectively.
Figure 4:
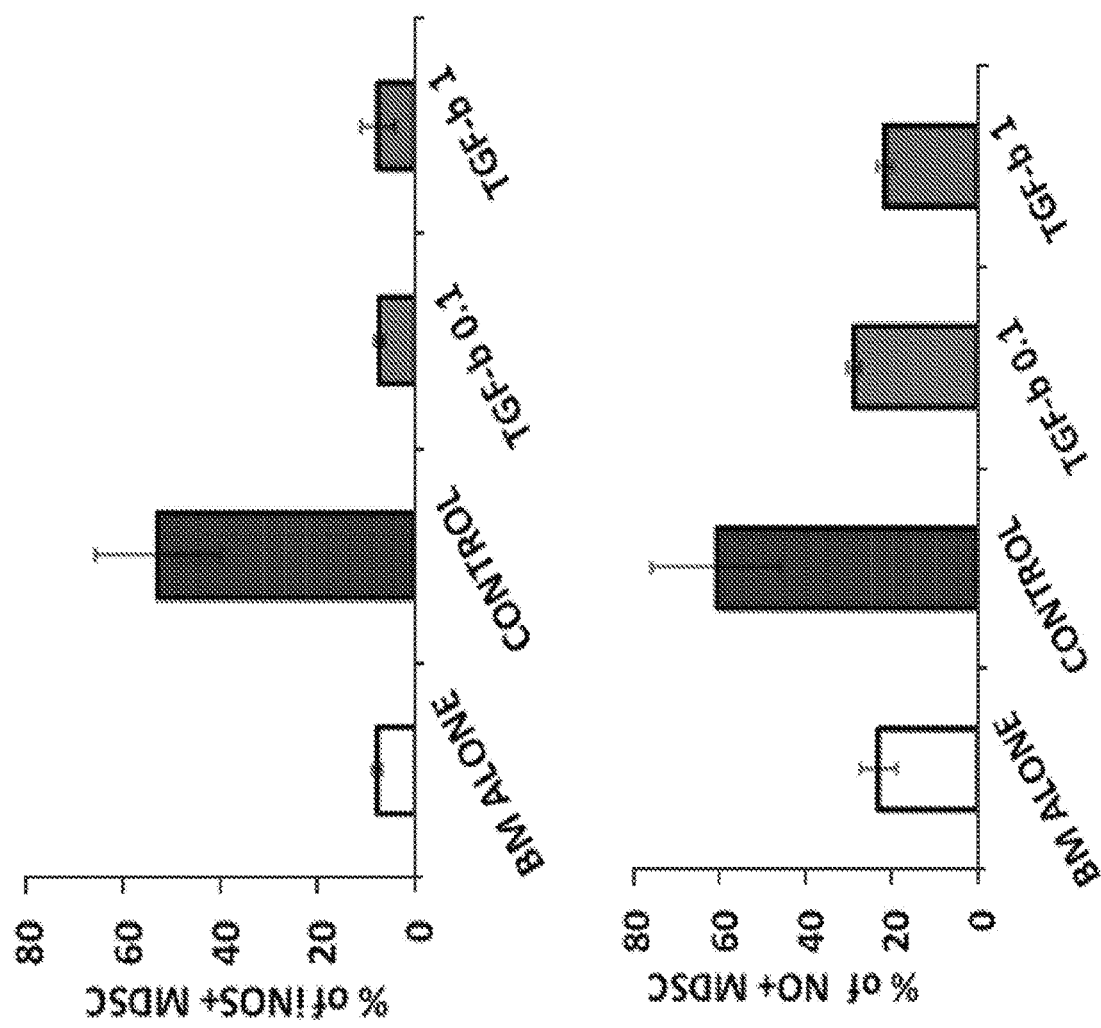
FIG. 4 illustrates the decrease of iNOS and NO in TGF-β primed MDSC that were derived with MT-RET melanoma supernatants. NO was measured by DAF-DA fluorescent assay.

As used herein, the use of the word "a" or "an" when used in conjunction with the term "comprising" in the claims and/or the specification may mean "one," but it is also consistent with the meaning of "one or more," "at least one," and "one or more than one." Some embodiments of the invention may consist of or consist essentially of one or more elements, method steps, and/or methods of the invention. It is contemplated that any method or composition described herein can be implemented with respect to any other method or composition described herein.

I. General Embodiments of the Disclosure

Embodiments of the disclosure include particular immune cells that have been modified from their original state to have an opposing action following exposure to one or more compositions. In particular embodiments, blood cells, bone marrow cells, or a mixture thereof are exposed to one or more cytokines, such as TGF-β1, in order for resultant differentiated cells to acquire anti-tumor activity and/or immune stimulatory activity. In particular embodiments, the blood cells, bone marrow cells, or a mixture thereof are also subjected to one or more events and/or to one or more conditions and/or to one or more compositions to differentiate into MDSCs. Such compositions may comprise one or more entities that generate the MDSC from the progenitor cells. In certain embodiments of the disclosure, mouse melanoma tumor supernatants and MTEC mouse head and neck squamous cell carcinoma (HNSCC) tumor supernatants (merely as examples) were utilized to generate MDSC in the presence or absence of TGF-β1.

MDSC are immunosuppressive bone-marrow-derived cells that suppress anti-tumor T cell responses, are observed in most if not all cancer types, and are a significant barrier to successful immunotherapy and contributors to tumor immune evasion. It is shown herein that 1) the immunosuppressive properties of MDSC, namely their ability to suppress T cell responses, can be reversed by inducing their development from bone marrow precursor cells in the presence of TGF-β1 ("TGF-β1-primed MDSC"), and in specific embodiments the TGF-β1 is recombinant; 2) TGF-β1-primed MDSC can enhance the proliferation of CD3/CD28 stimulated T cells; 3) TGF-β1-primed MDSC acquire anti-tumor activity against cancer cells grown in 2D and 3D (spheroid) culture. Overall similar findings are observed when TGF-β1-primed MDSC are derived from mouse bone marrow or human peripheral blood cells, as examples. These findings support useful therapeutic approaches to cancer such as at least the following: harvest of bone marrow or blood cells from an individual, generation of TGF-β1-primed MDSC, and adoptive transfer of these cells back into the individual (for example, through intratumoral or intravenous injection). Adoptive transfer of autologous TGF-β1-primed MDSC could be performed alone or in combination with other techniques, including other immunotherapeutic techniques (e.g., therapeutic tumor vaccination, checkpoint inhibition, etc.). This novel approach to adoptive immunotherapy is applicable to diverse cancer types.

Certain embodiments of the disclosure concern characterizing the anti-tumor utility of TGF-β1 primed cells, including at least TGF-β1 primed myeloid-derived suppressor cells (MDSC). As an example of methods of analysis, cellular analysis was performed by using flow cytometry assessment of one or more particular MDSC functional markers (such as iNOS, nitric oxide (NO), reaction oxygen species (ROS), arginase (ARG), PD-1 and PD-L1). MDSC were then co-cultured with human or mouse tumor cell lines in 2D or 3D (spheroid) culture to assess impact of TGF-β1 primed MDSC on tumor cell viability.

II. Cells of the Disclosure and Differentiation Embodiments

The disclosure utilizes particular MDSC immune cells for therapy for an individual, including for cancer therapy. The cells are of mammalian origin and may be of human origin. The MDSC immune cells may be generated by a skilled artisan or they may be commercially obtained. Methods of the disclosure may include the generation of the MDSCs in addition to their use in therapy. In particular embodiments wherein the generation of the MDSCs and their use are part of a method, the entity that generates the MDSCs is the same entity that utilizes them for therapy. In other embodiments, separate entities may generate the MDSCs and then utilize them for therapy.

In particular embodiments, progenitor cells (including at least bone marrow cells, blood cells (either peripheral blood or umbilical cord blood cells), or a mixture thereof) or tumor-resident immature myeloid cells are exposed to one or more events and/or to one or more conditions and/or to one or more compositions such that the progenitor cells differentiate into MDSCs. One of skill in the art recognizes which suitable events, conditions, and/or compositions would result in this differentiation, although in specific embodiments the progenitor cells differentiate into MDSCs upon exposure to one or more compositions that induce the differentiation of the bone marrow cells and/or blood cells to MDSCs. In specific embodiments, the one or more compositions comprises supernatant from cancer cells, one or more cytokines, or a combination thereof.

In embodiments to differentiate the bone marrow cells and/or blood cells to MDSCs, the bone marrow and/or blood cells are exposed to an effective amount of supernatant from any kind of cancer cells. The supernatant may be from one type of cancer cell or it may be from two or more types of cancer cells. The supernatant may be from cancer cells from the individual being treated or may be from research practices or may be commercially obtained. In specific embodiments, the supernatant comprises one or more compositions that facilitate differentiation of bone marrow cells and/or blood cells to MDSCs. In specific embodiments, the one or more compositions are cytokines. In some cases, the cytokines are produced endogenously from the cell, including produced from nucleic acids that are naturally endogenous to the cell. In some embodiments, the cancer cells from which the supernatant is obtained are modified, such as recombinantly engineered. In specific embodiments, the supernatant is obtained from cells that are engineered to express one or more compositions that facilitate differentiation of bone marrow cells and/or blood cells to MDSCs, such as wherein the cell harbors a vector that expresses the one or more compositions. The vector may be of any kind, including plasmid or viral, such as retroviral, lentiviral, adenoviral, adeno-associated viral, and so forth. Tumor cells may be engineered to express any of the many cytokines or inflammatory mediators known to induce MDSC from bone marrow precursors, including but not limited to one or more of the following: IL-6, VEGF, IL-1, GM-CSF, M-CSF, TNF-α, Prostaglandin E2. In such cases, cytokines present in the supernatant may be produced from the expression vectors in the cell and not from endogenous naturally occurring cytokine-expressing nucleic acids. In other cases, the supernatant comprises a mix of cytokines from endogenous nucleic acids and expression vector(s).

In some embodiments to differentiate the bone marrow cells and/or blood cells to MDSCs, the bone marrow and/or blood cells are exposed to one or more cytokines that are not comprised within a cell supernatant. The cytokine(s) may be of any kind, but in specific embodiments the cytokine(s) are IL-6, VEGF, IL-1, GM-CSF, M-CSF, TNF-α, and/or Prostaglandin E2. The one or more cytokines may be recombinant and may be produced by the hand of man. The one or more cytokines may be purified, such as from cells that produce or overproduce them.

Other factors that may be utilized to facilitate differentiation of bone marrow cells and/or blood cells to MDSCs include the following: cleavable cell membrane proteins; small molecule signaling mediators, such as ATP or adenosine; nucleic acids including DNA and various breakdown products of DNA; RNA, including microRNA and long non-coding RNA; various electrolytes and/or metabolic products of tumor cells; small secreted peptides; tumor-derived exosomes and the contents of these exosomes, including intracellular and membrane-associated cellular components, or a combination thereof.

In specific embodiments, the exposure of the progenitor cells to a certain one or more events and/or to one or more conditions and/or to one or more compositions to differentiate into MDSCs is the same exposure to one or more events and/or to one or more conditions and/or to one or more compositions to render the MDSCs to exhibit anti-tumor activity and/or immune stimulatory activity.

In certain cases, the blood cells and/or bone marrow cells are obtained as part of the method of the disclosure, and routine steps may be taken to achieve same. The blood cells and/or bone marrow cells that ultimately differentiate into the MDSCs may come from the individual being treated or may be otherwise obtained and utilized. In specific embodiments, peripheral blood mononuclear cells (PBMCs) are utilized in methods of the disclosure. PBMCs may be obtained by leukapheresis, for example.

In embodiments wherein blood cells and/or bone marrow cells are exposed to one or more compositions (either to differentiate into MDSC and/or to induce anti-tumor activity and/or immune stimulatory activity in resultant MDSC), the exposure step(s) may have any suitable duration. The duration of exposure may be on the order of minutes, hours, days, weeks, or months. In a specific embodiment the duration of exposure is at least or no more than 72 hours to 7 days. The duration of exposure may be at least or no more than 3-6, 3-5, 3-4, 4-7, 4-6, 4-5, 5-7, 5-6, or 6-7 days in length. In specific embodiments, the exposure step(s) are days long, such as at least or no more than 0.5, 1, 2, 3, 4, 5, 6, or 7 or more days. The exposure step(s) may be at least or no more than 1, 2, 3, 4, 5, 6, 7, 8, 9, 10, 11, 12, 13, 14, 15, 16, 17, 18, 19, 20, 21, 22, 23, or 24 hours long. The exposure step(s) may be at least or no more than 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, or 52 weeks. The exposure step(s) may be at least or no more than 1, 2, 3, 4, 5, 6, 7, 8, 9, 10, 11, or 12 months.

In cases wherein blood cells and/or bone marrow cells are exposed to one or more compositions to differentiate into MDSC and are exposed to one or more compositions to induce anti-tumor activity and/or immune stimulatory activity, such exposure steps may occur at the same time, at substantially the same time, may have overlap in time, or may be in succession. In cases wherein the two exposures are in succession, the exposure steps may occur in either order.

As used herein, the terms "cell," "cell line," and "cell culture" may be used interchangeably. All of these terms also include their progeny, which is any and all subsequent generations. It is understood that all progeny may not be identical due to deliberate or inadvertent mutations. In certain embodiments wherein a cell may express a heterologous nucleic acid sequence, "host cell" refers to a eukaryotic cell that is capable of replicating a vector and/or expressing a heterologous gene encoded by a vector. A host cell can be, and has been, used as a recipient for vectors. A host cell may be "transfected" or "transformed," which refers to a process by which exogenous nucleic acid is transferred or introduced into the host cell. A transformed cell includes the primary subject cell and its progeny. As used herein, the terms "engineered" and "recombinant" cells or host cells are intended to refer to a cell into which an exogenous nucleic acid sequence, such as, for example, a vector, has been introduced. Therefore, recombinant cells are distinguishable from naturally occurring cells that do not contain an introduced recombinant nucleic acid.

Depending upon the nature of the cells, the cells may be introduced into a host organism, e.g., a mammal, in a wide variety of ways. The cells may be introduced at the site of the tumor, in specific embodiments, although in alternative embodiments the cells hone to the cancer or are modified to hone to the cancer. The number of cells that are employed will depend upon a number of circumstances, the purpose for the introduction, the lifetime of the cells, the protocol to be used, for example, the number of administrations, the ability of the cells to multiply, the stability of the recombinant construct, and the like. The cells may be applied as a dispersion, generally being injected at or near the site of interest. The cells may be in a physiologically-acceptable medium. In specific embodiments, the cells are provided by intratumoral or intravenous injection. Cells may also be injected intralymphatically (into the draining or other lymph nodes), intra-aterially into feeder vessels supplying a diseased organ, intradermally adjacent to a cutaneous, mucosal or subcutaneous malignancy, or intraperitoneally, or intrathecally, for example.

In particular embodiments, cells that are produced by methods of the disclosure are isolated from their natural environment. Cells produced by methods encompassed herein may be modulated such that they are no longer identical or no longer substantially similar to those that exist in nature. Cells of the disclosure, having been modified upon exposure to particular conditions (including artificial conditions that are not identical to those found in nature), may be considered to be engineered by the hand of man. In specific cases at least, naturally existing cells are exposed to man-made conditions that result in the naturally existing cells becoming a different type of cell altogether. These cells may potentially be distinguished by unique combinations of cell surface markers, transcription factor expression/activation profiles, gene expression profiles, epigenomic modifications, or any combination of these attributes. Cells of the disclosure cannot exist in nature because in nature MDSC play a primarily immune suppressive role and do not comprise anti-tumor activity and/or immune stimulatory activity.

III. TGF-β1 Compositions

In embodiments of the disclosure, effective amounts of TGF-β1 are provided to a plurality of blood cells and/or bone marrow cells to generate MDSC that comprise anti-tumor activity and/or immune stimulatory activity. In particular embodiments, the TGF-β1 facilitates differentiation of blood cells and/or bone marrow cells to MDSC and also facilitates imparting anti-tumor activity and/or immune stimulatory activity to the resultant MDSC that otherwise would not have anti-tumor activity and/or immune stimulatory activity.

In specific embodiments, the TGF-β1 may be human TGF-β1, although in some cases it is rat or mouse TGF-β1. Although the skilled artisan is aware how to obtain sequences for TGF-β1, an example of a protein sequence is at GenBank® Accession No. NP_000651.3 GI:63025222, and an example of a nucleotide sequence is at GenBank® Accession No. NM_000660.6 GI:1049749421.

In particular embodiments, the entire protein of TGF-β1 is provided to cells, wherein in specific embodiments only part of the protein sequence of TGF-β1 is provided to cells. In embodiments wherein a part of the protein sequence is provided, the sequence may comprise a domain for cytokine activity, a domain for protein binding, a glycosylation domain, a ubiquitination domain, and a combination thereof. TGF-β1 may be provided as a homodimer, a precursor molecule including propeptide region, in multimolecular complex with the latent TGFB binding protein, and/or the fully cleaved and processed moiety. TGF-β1 activity can occur when the molecule is soluble, or when membrane-bound. In specific cases, the protein is missing the C-terminus, the N-terminus, or both.

The amount of TGF-β1 that is provided to the cells may be of any suitable amount, but in particular embodiments the concentration is in an amount of 1 ng/ml through 10 ng/ml. The concentration may be at least or no more than a range of 1-9, 1-8, 1-7, 1-6, 1-5, 1-4, 1-3, 1-2, 2-10, 2-9, 2-8, 2-7, 2-6, 2-5, 2-4, 2-3, 3-10, 3-9, 3-8, 3-7, 3-6, 3-5, 3-4, 4-10, 4-9, 4-8, 4-7, 4-6, 4-5, 5-10, 5-9, 5-8, 5-7, 5-6, 6-10, 6-9, 6-8, 6-7, 7-10, 7-9, 7-8, 8-10, 8-9, or 9-10 ng/ml. The concentration may be at least or no more than 0.5, 1, 1.25, 1.5, 1.75, 2, 2.25, 2.5, 2.75, 3, 3.25, 3.5, 3.75, 4, 4.25, 4.5, 4.75, 5, 5.25, 5.5, 5.75, 6, 6.25, 6.5, 6.75, 7, 7.25, 7.5, 7.75, 8, 8.25, 8.5, 8.75, 9, 9.25, 9.5, 9.75, or 10 ng/ml. In some cases, one or more additional doses (of the same or different amount) may be provided to the culture after a certain amount of time.

IV. Examples of Methods of Treatment

MDSC exposed to TGF-β1 upon their differentiation may be provided to an individual in need thereof. In specific embodiments, the individual has cancer. The cancer may be of any kind, but in specific embodiments the cancer is lung, breast, colon, prostate, pancreatic, stomach, blood, gall bladder, spleen, rectal, skin, brain, bone, liver, head and neck, thyroid, pituitary gland, uterine, testicular, cervical, ovarian, lymphoma, leukemia, and so forth. The cancer may be metastatic. The cancer may be refractory to one or more treatments. The individual may be diagnosed with cancer, and the cancer may be of any stage.

The MDSC of the disclosure may be suspended in a pharmaceutically acceptable carrier upon delivery to an individual in need thereof. As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the pharmaceutical compositions is contemplated.

In some embodiments, an individual known to have cancer is subject to blood and/or bone marrow removal, and the blood and/or bone marrow are processed such that cells from them are suitable for culture. The cells may be cultured in the presence of TGF-β1 and, in some cases, also at least one composition that induces the cells to become MDSC, for a suitable length of time and suitable conditions such that the produced MDSC comprise anti-tumor activity and/or immune stimulatory activity. In other cases, commercial bone marrow and/or blood cells (such as PBMCs) are obtained and are put into culture for differentiation to MDSC.

In alternative embodiments, the MDSCs of the disclosure are provided to an individual with a medical condition other than cancer, given their immune stimulatory activity.

V. Combination Therapies

In some cases, the TGF-β1-primed MDSC are provided as a cancer therapy in need thereof and, optionally, in addition to another cancer therapy. In cases wherein the TGF-β1-primed MDSC are provided as a cancer therapy with another cancer therapy, the other cancer therapy may be of any kind. In certain embodiments, the additional cancer therapy encompasses at least surgery, radiation, chemotherapy, immunotherapy, gene therapy, therapy with small molecule inhibitors or other examples of molecular targeted therapy, hormone therapy, a combination thereof, and so forth. When one or more combination therapies are used in conjunction with the therapy of the disclosure, they may be provided at the same or different times, or there may be some overlap in time. In some embodiments, the therapy of the present disclosure is provided to an individual prior to another cancer therapy, whereas in other embodiments the therapy of the present disclosure is provided to an individual subsequent to another cancer therapy.

The present inventive therapy may precede or follow the other agent treatment by intervals ranging from minutes to weeks. In embodiments where the other agent and present disclosure are applied separately to the individual, one would generally ensure that a significant period of time did not expire between the time of each delivery, such that the agent and inventive therapy would still be able to exert an advantageously combined effect on the cell. In such instances, it is contemplated that one may contact the cell with both modalities within about 12-24 hours of each other and, more preferably, within about 6-12 hours of each other. In some situations, it may be desirable to extend the time period for treatment significantly, however, where several d (2, 3, 4, 5, 6 or 7) to several weeks (1, 2, 3, 4, 5, 6, 7 or 8) lapse between the respective administrations.

The TGF-β1-primed MDSC may precede, be co-current with and/or follow the other agent(s) by intervals ranging from minutes to weeks. In embodiments where the TGF-β1-primed MDSC, and other agent(s) are applied separately to a cell, tissue or organism, one would generally ensure that a significant period of time did not expire between the time of each delivery, such that the TGF-β1-primed MDSC and agent(s) would still be able to exert an advantageously combined effect on the cell, tissue or organism. For example, in such instances, it is contemplated that one may contact the cell, tissue or organism with two, three, four or more modalities substantially simultaneously (i.e. within less than about a minute) as the TGF-β1-primed MDSC. In other aspects, one or more agents may be administered within from substantially simultaneously, about 1 minute, about 5 minutes, about 10 minutes, about 20 minutes about 30 minutes, about 45 minutes, about 60 minutes, about 2 hours, about 3 hours, about 4 hours, about 5 hours, about 6 hours, about 7 hours about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 22 hours, about 23 hours, about 24 hours, about 25 hours, about 26 hours, about 27 hours, about 28 hours, about 29 hours, about 30 hours, about 31 hours, about 32 hours, about 33 hours, about 34 hours, about 35 hours, about 36 hours, about 37 hours, about 38 hours, about 39 hours, about 40 hours, about 41 hours, about 42 hours, about 43 hours, about 44 hours, about 45 hours, about 46 hours, about 47 hours, about 48 hours, about 1 day, about 2 days, about 3 days, about 4 days, about 5 days, about 6 days, about 7 days, about 8 days, about 9 days, about 10 days, about 11 days, about 12 days, about 13 days, about 14 days, about 15 days, about 16 days, about 17 days, about 18 days, about 19 days, about 20 days, about 21 days, about 1, about 2, about 3, about 4, about 5, about 6, about 7 or about 8 weeks or more, and any range derivable therein, prior to and/or after administering the TGF-β1-primed MDSC.

Combination anti-cancer agents that may be used with the TGF-β1-primed MDSC include, for example, acivicin; aclarubicin; acodazole hydrochloride; acronine; adozelesin; aldesleukin; altretamine; ambomycin; ametantrone acetate; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; celecoxib (COX-2 inhibitor); chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; ilmofosine; iproplatin; irinotecan; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; taxotere; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride; 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidenmin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; doxorubicin; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imatinib (e.g., GLEEVEC®), imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin;

levamisole; liarozole; linear polyamine analogue; lipophilic disaccharide peptide; lipophilic platinum compounds; lissoclinamide 7; lobaplatin; lombricine; lometrexol; lonidamine; losoxantrone; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mitoguazone; mitolactol; mitomycin analogues; mitonafide; mitotoxin fibroblast growth factor-saporin; mitoxantrone; mofarotene; molgramostim; Erbitux, human chorionic gonadotrophin; monophosphoryl lipid A+myobacterium cell wall sk; mopidamol; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin: neridronic acid; nilutamide; nisamycin; nitric oxide modulators; nitroxide antioxidant; nitrullyn; oblimersen (GENASENSE®); O.sup.6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RH retinamide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stipiamide; stromely sin inhibitors; sulfinosine; superactive vasoactive intestinal peptide antagonist; suradista; suramin; swainsonine; tallimustine; tamoxifen methiodide; tauromustine; tazarotene; tecogalan sodium; tegafur; tellurapyrylium; telomerase inhibitors; temoporfin; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; velaresol; veramine; verdins; verteporfin; vinorelbine; vinxaltine; vitaxin; vorozole; zanoterone; zeniplatin; zilascorb; and zinostatin stimalamer, or any analog or derivative variant of the foregoing and also combinations thereof. In specific embodiments, chemotherapy for the individual is employed in conjunction with the disclosure, for example before, during and/or after administration of the disclosure.

Other cancer therapies that may be used in conjunction with the cells of the disclosure include γ-rays, X-rays, and/or the directed delivery of radioisotopes to tumor cells, in addition to microwaves and UV-irradiation. Dosage ranges for X-rays (for example) range from daily doses of 50 to 200 roentgens for prolonged periods of time (3 to 6 wk), to single doses of 2000 to 6000 roentgens. Dosage ranges for radioisotopes vary widely, and depend on the half-life of the isotope, the strength and type of radiation emitted, and the uptake by the neoplastic cells.

Immunotherapeutics that rely on the use of immune effector cells and molecules (such as small molecules and/or macromolecules/biologics) to target and destroy cancer cells and that are other than the cells of the disclosure may be used, in certain embodiments. The immune effector may be, for example, an antibody specific for some marker on the surface of a tumor cell. The antibody alone may serve as an effector of therapy or it may recruit other cells to actually effect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include macrophages, dendritic cells, cytotoxic T cells, "helper" CD4 T cells, NK cells, NKT cells, and engineered (chimeric antigen receptor—CAR) versions of each of these different cell types. Immunotherapies may also include various strategies for vaccination, including all combinations of peptide, protein and DNA or RNA antigens or the molecules coding same (including vaccination with DNA sequences encoding target antigens); including vaccination approaches based on manipulation of dendritic cells or other antigen-presenting cells; including all manner of specific and non-specific adjuvants including cytokines, so-called danger signals (including agonists of toll-like receptors and other so-called danger-associated molecular patterns (DAMPs), and including chemical or physical adjuvants with or without specific tumor antigen, such antigen also potentially provided through destruction or normal turnover of tumor cells.

VI. Kits of the Disclosure

Any of the compositions described herein may be comprised in a kit. In a non-limiting example, cells, cytokines, and/or other reagents may be comprised in a kit.

The kits may comprise suitably aliquoted cell or other compositions of the present disclosure. The components of the kits may be packaged either in aqueous media or in lyophilized form. The container means of the kits will generally include at least one vial, test tube, flask, bottle, syringe or other container means, into which a component may be placed, and preferably, suitably aliquoted. Where there are more than one component in the kit, the kit also will generally contain a second, third or other additional container into which the additional components may be separately placed. However, various combinations of components may be comprised in a vial. The kits of the present invention also will typically include a means for containing the compositions in close confinement for commercial sale. Such containers may include injection or blow-molded plastic containers into which the desired vials are retained. In specific embodiments, the kit comprises one or more means for obtaining blood cells and/or bone marrow cells.

When the components of the kit are provided in one and/or more liquid solutions, the liquid solution is an aqueous solution, with a sterile aqueous solution being particularly preferred. The compositions may also be formulated into a syringeable composition. In which case, the container means may itself be a syringe, pipette, and/or other such like apparatus, from which the formulation may be applied to an infected area of the body, injected into an animal, and/or even applied to and/or mixed with the other components of the kit. However, the components of the kit may be provided as dried powder(s). When reagents and/or components are provided as a dry powder, the powder can be reconstituted by the addition of a suitable solvent. It is envisioned that the solvent may also be provided in another container means.

EXAMPLES

The following examples are included to demonstrate preferred embodiments of the inventions. It should be appreciated by those of skill in the art that the techniques disclosed in the examples which follow represent techniques discovered by the inventor to function well in the practice of the inventions, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the inventions.

Example 1

TGF-β1 Primed Murine Myeloid Derived Suppressor Cells Lose Their Ability to Suppress T Cell and Decrease Tumor Growth Myeloid derived suppressor cells (MDSC) consist of myeloid progenitor and immature cells, which are recruited to the tumor site by cancer-related inflammation. Conventional MDSC's suppress T cell proliferation and promote tumor growth/angiogenesis by various mechanisms, and functional maturation of MDSC depends on iNOS-produced nitric oxide (NO). TGF-β1 is a pleiotropic cytokine abundantly expressed in the tumor microenvironment with diverse effects on myeloid, lymphoid and tumor cells. In many situations, TGF-β1 is highly immunosuppressive. In specific embodiments, the effect of TGF-β1 in the generation and function of MDSC is determined, including its effects on T cell proliferation and tumor growth.

Methods:

Ex vivo MDSC generation: Bone marrow progenitor cells were derived from WT C57bl/6 mice and cultured in the presence of MTEC (transformed murine pharyngeal epithelial cells expressing HPV E6, E7, and ras oncogenes) tumor supernatants±TGF-β1 for 5 days at 37° C. Cells were then harvested, processed into single cell suspensions, and stained for MDSC surface markers, NO by DAF-DA, iNOS and other functional markers and analyzed using flow cytometry.

T cell proliferation assay MDSCs were generated±TGF-β1 with supernatants from MTEC cells and co-cultured with CFSE labeled T cells activated with anti CD3 & anti CD28 antibodies. T cell proliferation was measured by using CFSE dilution, which was analyzed by flow cytometry.

Effect of MDSC on tumor growth Control and TGF-β1 conditioned MDSC were co-cultured with murine (MTEC) or human (T-hep3) head and neck cell lines (grown as spheroids or monolayer) for 72 hrs at the end of which proliferation of the spheroid was assessed using Ki-67 or tumor numbers was determined by flow cytometry of single cell suspensions.

Results:

TGF-β1 primed MDSC's failed to inhibit T cell proliferation compared to control MDSC. Further, TGF-β1 primed MDSC inhibited tumor growth in an ex vivo co-culture system. The spheroids co-cultured with TGF-β1 conditioned MDSC revealed decreased ki-67 expression compared to control. It was also seen that TGF-β1 treated MDSC's down regulate both iNOS and NO expression compared to control MDSC while not altering the expression of other MDSC functional markers like Arginase, and (in the case of murine MDSC) PD-1 and PD-L1.

Therefore, TGF-β1 reprograms MDSC to a) decrease their ability to suppress T cells; and b) directly suppress tumor cell growth. These observations have a direct translational implication wherein the inherent pro-tumor nature of MDSCs can be reprogrammed with TGF-β1 and directed against the tumor.

Example 2

Effect of TGF-β1 on Human Myeloid Derived Suppressor Cells (MDSC)

Myeloid derived suppressor cells (MDSC) are a heterogeneous population of myeloid progenitor cells and immature myeloid cells. MDSC plays an important role in tumor-mediated immunosuppression. MDSCs mediate T cell suppression through a variety of mechanisms, including arginase-1 (ARG-1)-mediated local arginine depletion, inducible NO synthase (iNOS) and NADPH oxidase (NOX2) production of reactive oxygen and nitrogen species, VEGF expression, and cysteine depletion. TGF-β1 is a pleiotropic cytokine abundantly expressed in the tumor microenvironment with diverse effects on myeloid, lymphoid and tumor cells. The aim of this study is to determine the effect of TGF-β1 in the generation and function of MDSC, including its effects on T cell proliferation and tumor growth.

Methods:

Generation of MDSC: PBMCs were derived from healthy individual and co-cultured with either cytokines (GM-CSF+ IL-6) or tumor supernatants (DHEP3 and SCC47) in the presence or absence of TGF-β1 for 6-7 days at 37° C. Cells were then harvested and stained for MDSC surface markers (CD33+CD11b+HLADR−); samples were acquired by flow cytometry. CD33+ cells were sorted either using beads or FACS.

T cell proliferation assay: MDSCs were generated in the presence or absence of TGF-β1 with cytokines or tumor supernatants and co-cultured with CFSE labeled T cells activated with anti CD3 and anti CD28 antibodies. T cell proliferation was measured by using CFSE dilution, which was analyzed by flow cytometry.

Effect of MDSC on tumor growth: Control and TGF-β1 conditioned MDSC were co-cultured with SCC47 human head and neck cancer cell line (grown as spheroids) for 72 hrs at the end of which histological sections of the spheroids were prepared and analyzed for tumor proliferation by Ki-67 staining and cleaved caspase assay.

Results:

While the percentage of human MDSC increases in presence of TGF-β1, TGF-β1 primed MDSC's lost the ability to inhibit T cell proliferation unlike control MDSC that suppressed T cell proliferation in dose dependent fashion.

Although TGF-β1 increases MDSC number phenotypically, it compromises T cell suppressive capacity. This observation has a direct translational implication wherein the inherent pro-tumor nature of MDSCs could potentially be reprogrammed with TGF-β1 and directed toward the tumor thereby suppressing tumor growth.

Additionally, the TGF-β1 primed MDSC develop an ability to suppress tumor cell growth, as evidenced by loss of spheroid integrity and decrease in proliferation marker Ki67, which is not present in conventionally-derived MDSC.

Example 3

Effect of TGF-β1 on MDSC Markers of Functional Activity, Anti-Tumor Activity, and Immunosuppressive Function in Ex-Vivo Culture FIG. 1 demonstrates cellular profile of control vs. TGF-β1 primed MDSCs. The top line horizontally is TGF-β1, the middle horizontal line is the control, and the bottom line horizontally is bone marrow (BM) alone.

Figure 5:
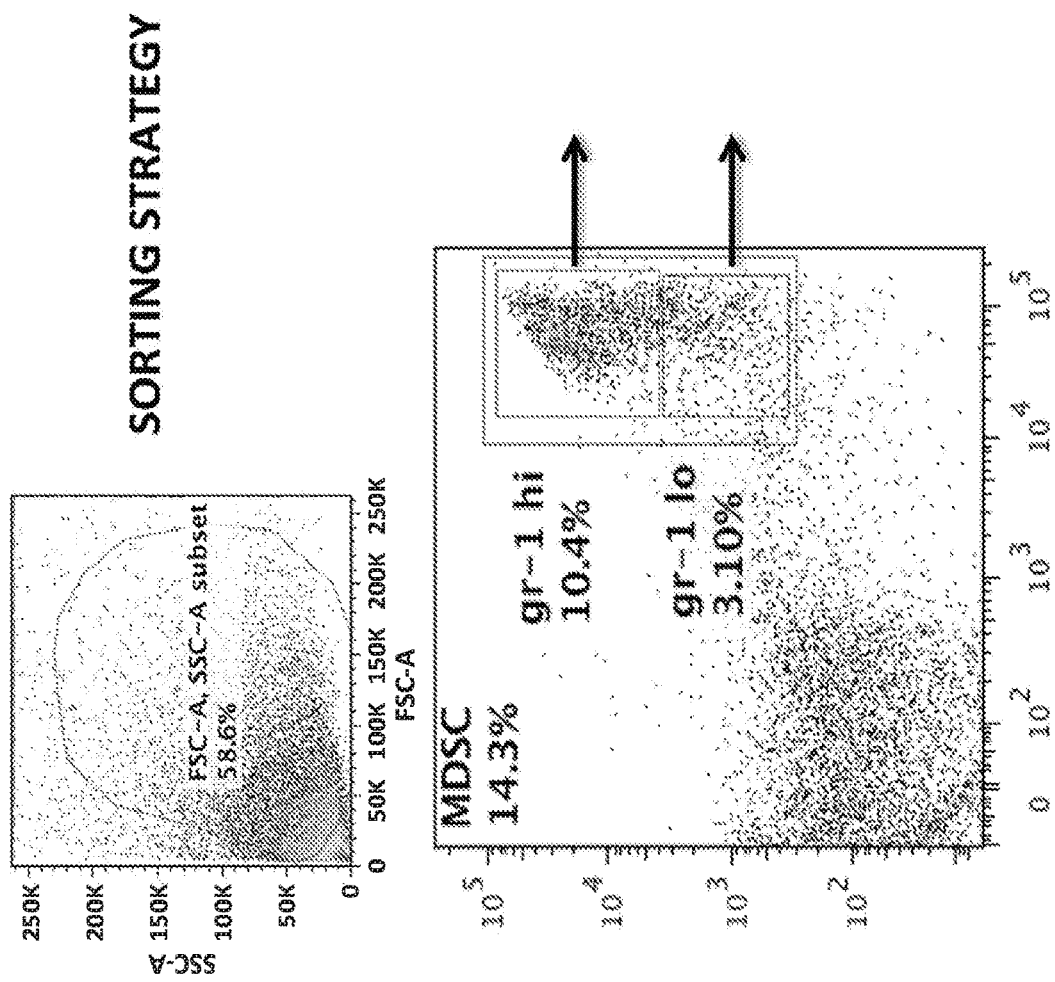
FIG. 5 shows a representative flow cytometry gating scheme for MDSCs derived from BM progenitors with tumor supernatants (in this example, MT-RET melanoma)

FIG. 5 shows the effect of exogenous TGF-β1 on generation and function of MDSCs derived from BM progenitors with tumor supernants (as examples, MT-RET melanoma and MTEC HNSCC). Briefly, for ex vivo studies BM cells were cultured with RET tumor supernatants for 4-5 days in the presence or absence of TGF-β1. The total MDSCs or Gr-1hi or lo fractions were sorted. The sorted cells were co-cultured with CFSE labeled T cells from wildtype mice and stimulated with anti-CD3+anti-CD28. T proliferation was measured by CFSE dilution by flow cytometry after 72 hours.

Figure 6:
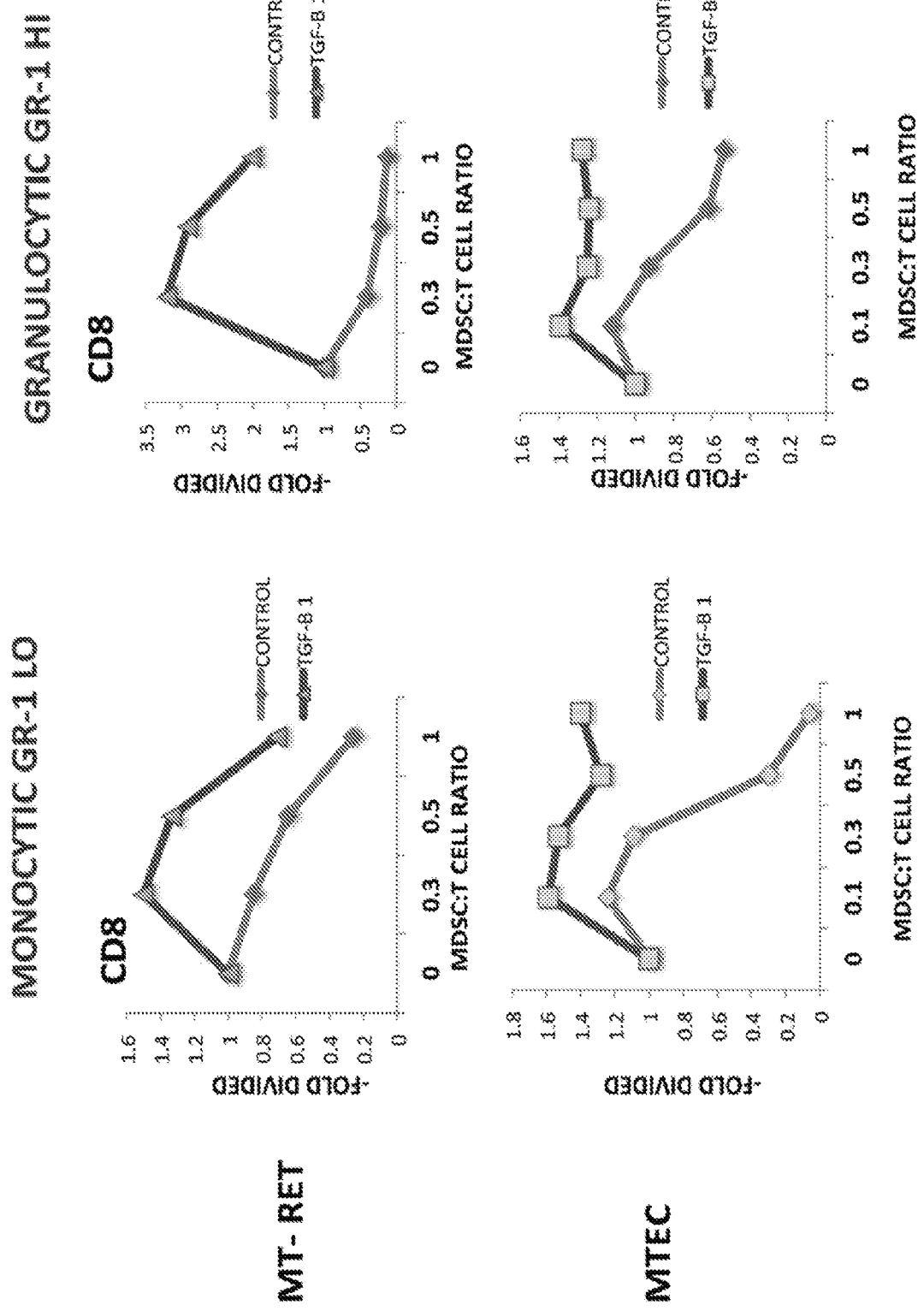
FIG. 6 shows that TGF-β primed MDSC are less suppressive than their control counterparts and, in specific embodiments, increase T cell proliferation.

FIG. 6 shows that TGF-β primed MDSC are less suppressive than their control counterparts and, in specific embodiments, increase T cell proliferation.

In certain embodiments, TGF-β1 alters the function of MDSC, making them anti-tumorigenic. The disclosure encompasses elucidation of the effect of TGF-β1 on MDSC generation and function, including the effect on T cell proliferation and homing to a tumor. The present disclosure encompasses the characterization of the effect of TGF-β1 conditioned MDSCs on tumor growth.

In particular embodiments, the TGF-β1 primed MDSC mediate decreased tumor growth and/or elicit tumor killing.

Models were employed in which there was co-culturing of tumor cells (monolayer or spheroid) with control and TGF-β1 primed MDSC for three days, followed by analysis of cell numbers by FACS or analysis of spheroids by Hematoxylin and eosin stain (H&E) staining and Ki67 (a representation of proliferation).

Figure 7:
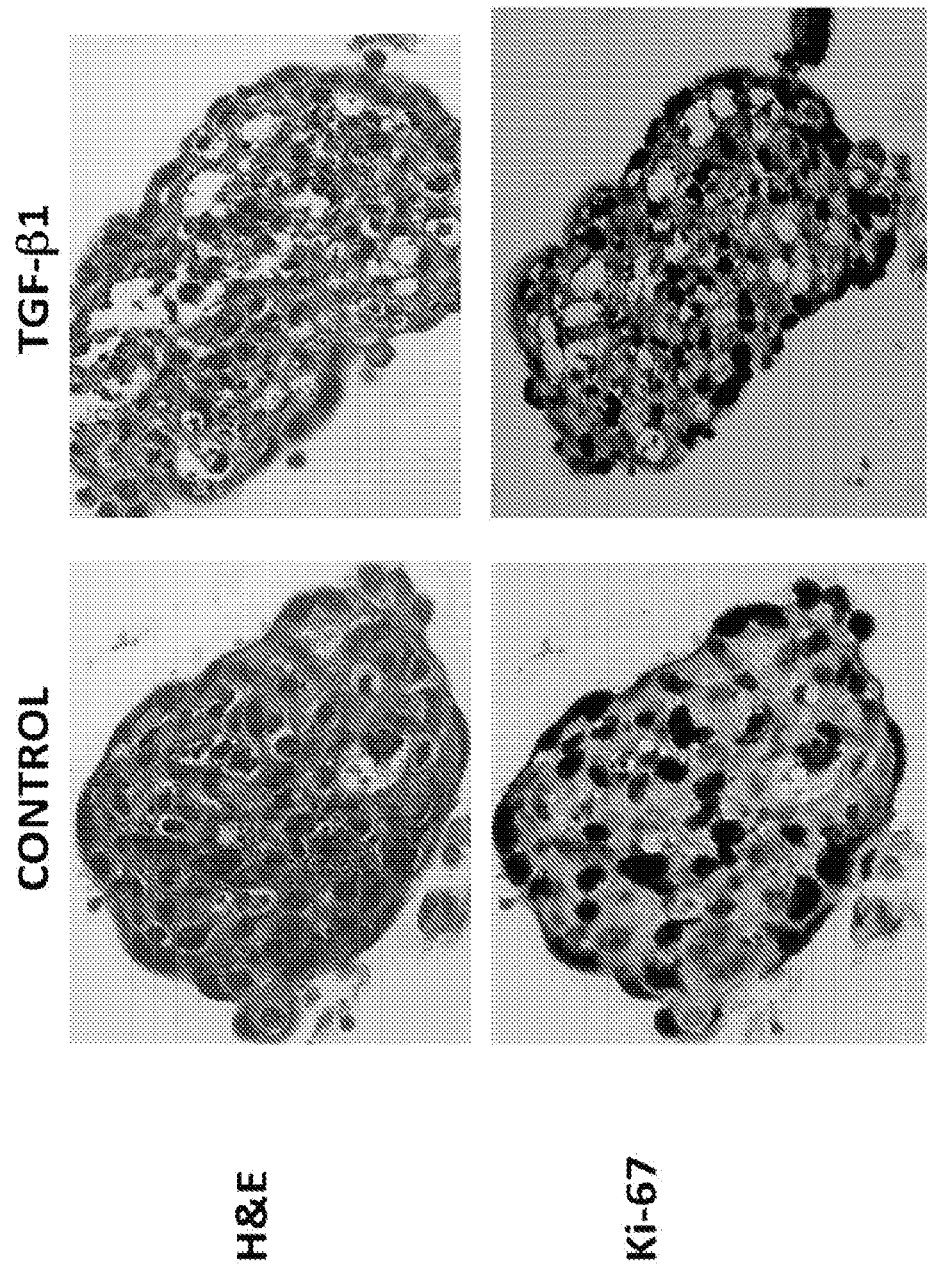
FIG. 7 demonstrates that TGF-β1-primed MDSC reduce tumor spheroid integrity and decrease proliferation.
Figure 8:
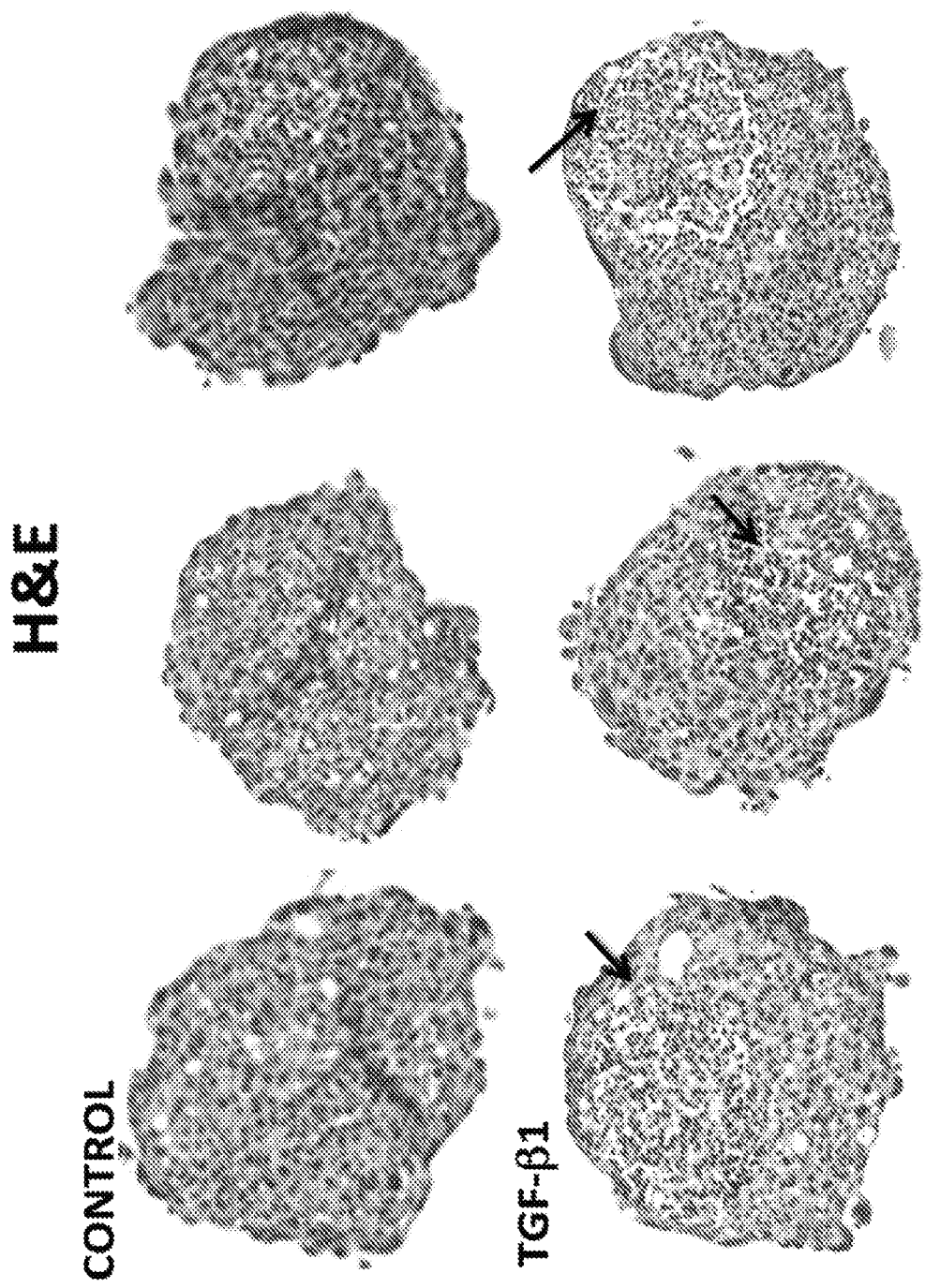
FIG. 8 shows H&E staining in control and TGF-β1-primed MDSC for multiple spheroids, again demonstrating decrease in spheroid integrity.
Figure 9:
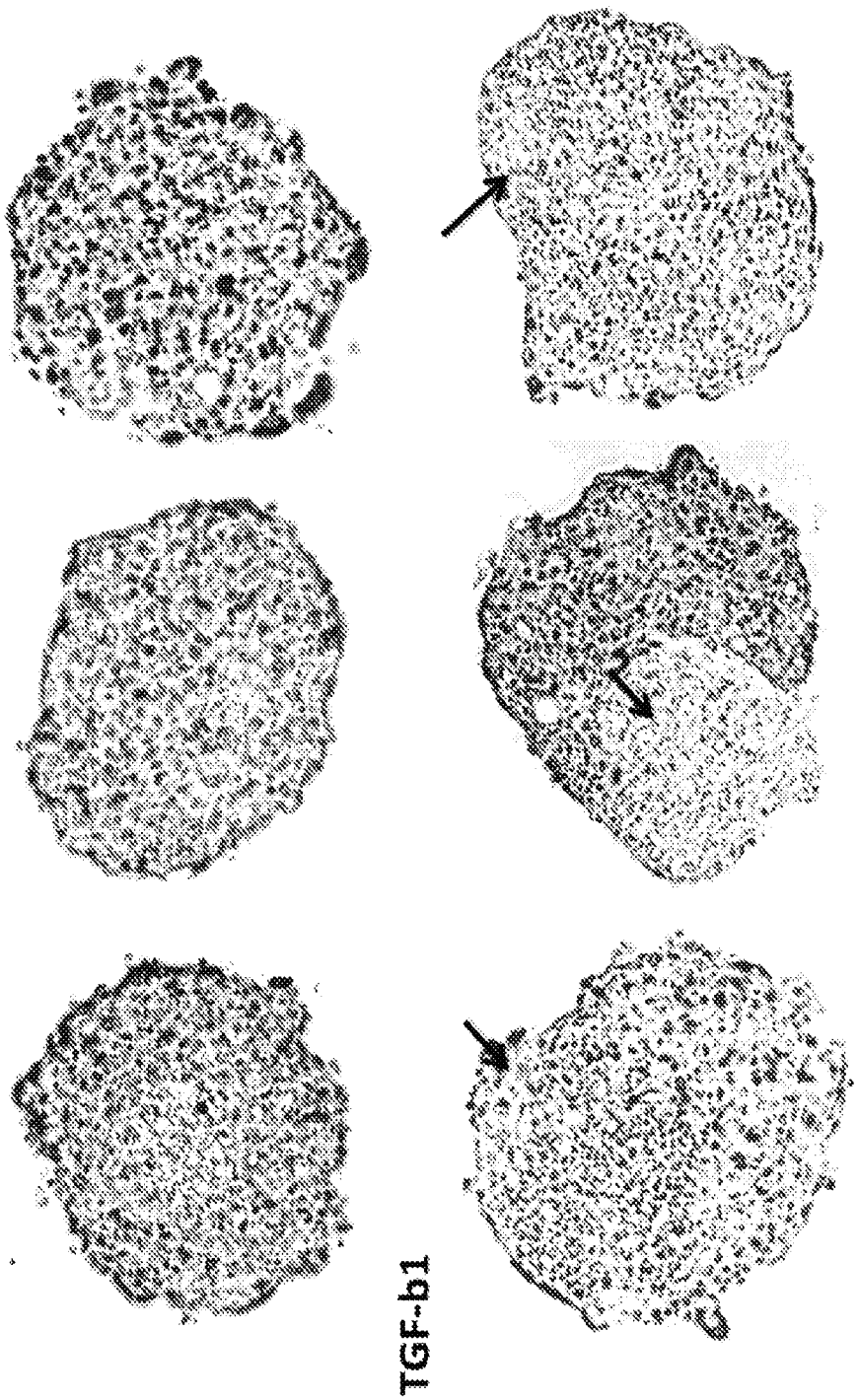
FIG. 9 shows Ki-67 (proliferation marker) immunohistochemistry in control and TGF-β1-primed MDSC.

FIG. 7 shows TGFβ-1 primed MDSCs reduce tumor spheroid integrity. FIG. 8 shows H&E staining of the spheroids. FIG. 9 shows Ki-67 staining (proliferation marker) for the spheroids of cells.

In embodiments of the disclosure, the addition of TGF-β1 during the generation of MDSC from tumor supernatants gives rise to "Reprogrammed MDSCs" that lose their ability to suppress T cell proliferation and acquire the ability to kill or suppress tumor growth. The expression of prod-MDSC markers such as iNOS and NO are significantly decreased in TGF-β1 primed MDSCs. In particular embodiments, TGF-β1 primed MDSCs can be delivered to a tumor to effect tumor killing without adversely affecting intratumoral immunity.

Example 4

Immune Stimulatory Function and Anti-Tumor Activity of TGF-β1 Primed Mouse MDSC

The present example shows immune stimulatory function and also anti-tumor activity in TGF-β1 primed mouse MDSC.

Examples of methods are as follows:
Generation of Murine MDSC
Bone marrow was flushed from the femur of naïve C57BL/6 and single cell suspensions were prepared. $5 \times 10^6$ total bone marrow cells were co-cultured with 30% v/v of MTEC-tumor supernatants in the presence or absence of 10 ng/ml of TGF-β1 for 4-5 days.
MDSC Isolation
a) Cells were harvested from control and TGF-β1 cultures. CD11b+ cells were then positively selected using the MACS militenyi beads according to the manufacturer's instructions to a purity of >95%.
b) MDSCs were sorted (using BD FACS ARIA) from control and TGF-β1 cultures using antibody against CD11b to a purity of >99%.
Cytology
Cytospin slides were derived from control and TGF-β1 CD11b+ cells and stained with giemsa to discern cell morphology.
MDSC Surface Staining and iNOS/NO Measurements
Murine MDSC were generated from naïve bone marrow cells co-cultured with MTEC tumor supernatants as described earlier. Cells were then harvested from control and TGF-β1 cultures and were first surface stained for MDSC using the antibodies against Gr-1 and CD11(ebiosciences) followed by DAF-DA (Sigma-Aldrich) to measure NO levels from MDSC.

iNOS was measured in MDSC by performing intracellular staining on cells surface stained with GR-1 and CD11-B (using eBiosciences fix/perm kit).

Cellular populations were analyzed using flow cytometry with BD LSRII.
T Cell Suppression Assay
MDSC were generated from murine bone marrow cells as described earlier. MDSC's were then sorted using anti-CD11b antibody from control and TGF-β1 groups as previously described. Control and TGF-β derived MDSC's were then co-cultured with CFSE labelled naïve spleen cells at various T cell:MDSC ratios (1:1, 1:0.5, 1:0.3 and 1:0.1) and activated with soluble anti-CD3 (1 ug/ml) and anti-CD28 (0.5 ug/ml) for 3 days. T cell proliferation was measured at the end of 3 days by CFSE dilution using flow cytometry.
Tumor Killing Assay
2D culture: MDSC's were generated by co-culture of murine C57bl/6 bone marrow cells with MTEC tumor supernatants, in the presence or absence of TGF-β1 as previously described. Resulting MDSC were. co-cultured with MTEC tumor cells at various tumor:MDSC ratios (1:1, 1:0.3 and 1:0.1) for 48 hrs. At the end of 48 hrs, cells were harvested and surface stained for CD45 to differentiate tumor cells (CD45-negative) from myeloid cells (CD45+) and apoptosis was evaluated using a combination of Annexin V and PI using flow cytometry.

3D Spheroid cultures: 3D MTEC tumor spheroids were generated using the hanging drop method. They were then co-cultured with MDSC's derived from control and TGF-β1 cultures for 3 days after which spheroid sections were submitted for histology. Proliferation was evaluated using Ki-67 and apoptosis using antibody to caspase-3 by IHC.

FAS-L Staining and Neutralization

MDSC's were generated and isolated from both control and TGF-β1 cultures as previously described and co-cultured with MTEC tumor cells at various tumor:MDSC ratios (1:1, 1:0.3 and 1:0.1). Cells were harvested at 0, 24 and 48 hrs and surface stained with anti-CD45 to differentiate tumor cells from myeloid cells, anti-CD11b, anti-F4/80 and anti-FAS L and analyzed by FACS.

For FAS-L neutralization studies, MDSC's derived from control and TGF-β1 cultures were incubated with blocking antibody to FAS L for 5 hours after which the cells were washed once and co-cultured with MTEC tumor cells at various ratios as described above and apoptosis was evaluated using Annexin V and PI stains in CD45-negative (tumor) cells.

In Vivo Tumor Growth Measurements with TGF-β1 MDSC

MDSC's were generated from murine bone marrow cells in the presence or absence of TGF-β1 and CD11b+ cells were isolated using positive selection by antibody-coated beads as described earlier.

0.8-1×10^6 MDSC's thus obtained from control and TGF-β1 cultures were intratumorally injected into MTEC-tumor bearing mice (palpable tumors) every 4-5 days for 15 days. Tumor growth curves were measured in the following groups of mice:

a) control MDSC
b) TGF-β1 MDSC

Histology was performed on tumor sections obtained from the above groups.

Intratumoral Injection of MDSC in Combination with Irradiation

MDSC's were generated from murine bone marrow cells in the presence or absence of TGF-β1 and CD11b+ cells were isolated using positive selection by Militenyi beads as described earlier.

Figure 10:
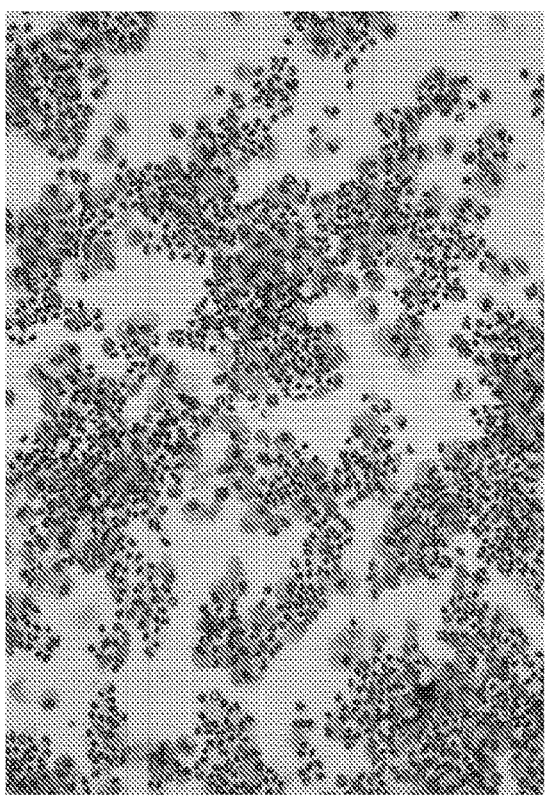
FIG. 10 shows TGF-β1 primed MDSC display more macrophage like cells then control MDSC.
Figure 10:
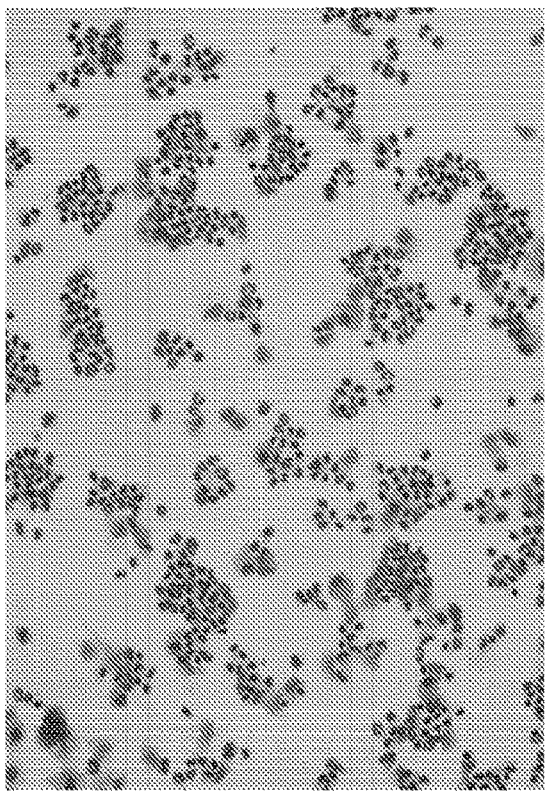

0.8-1×10^6 MDSC's obtained from control and TGF-β1 cultures were intra tumorally injected into MTEC-tumor bearing mice (palpable tumors) every 4-5 days for 15 days along with 2 doses of 15 GY tumor-directed irradiation administered via an external beam. Tumor growth curves were measured in the following groups of mice:

a) no treatment
b) 30 GY irradiation alone
c) 30 GY+control MDSC
d) 30 GY+TGF-β1 MDSC TGFβ Alters the Phenotype of Myeloid-Derived Suppressor Cells TGF-β1 primed MDSC display more macrophage like cells then control MDSC As shown in FIG. 10 murine bone marrow cells were cultured with tumor supernatants in the presence or absence of TGFβ to produce MDSC. CD11b+ cells were sorted and subjected to geimsa staining to evaluate cellular morphology. MDSC created in the presence of TGFβ display an increased number of macrophage/histiocyte-like cells.

Figure 11:
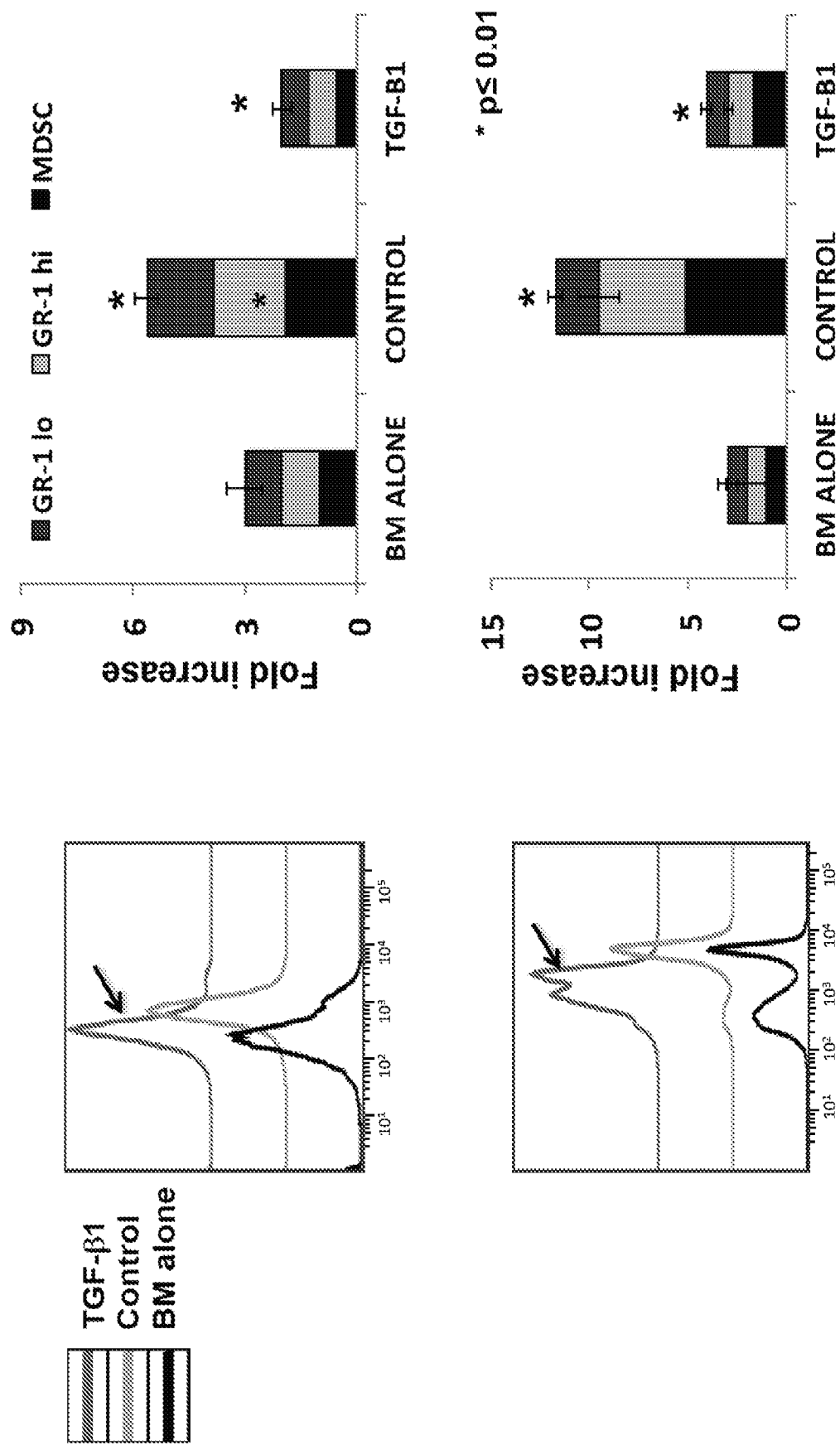
FIG. 11 demonstrates that TGF-β1 significantly decreases iNOS and NO expression in MDSC.
Figure 12:
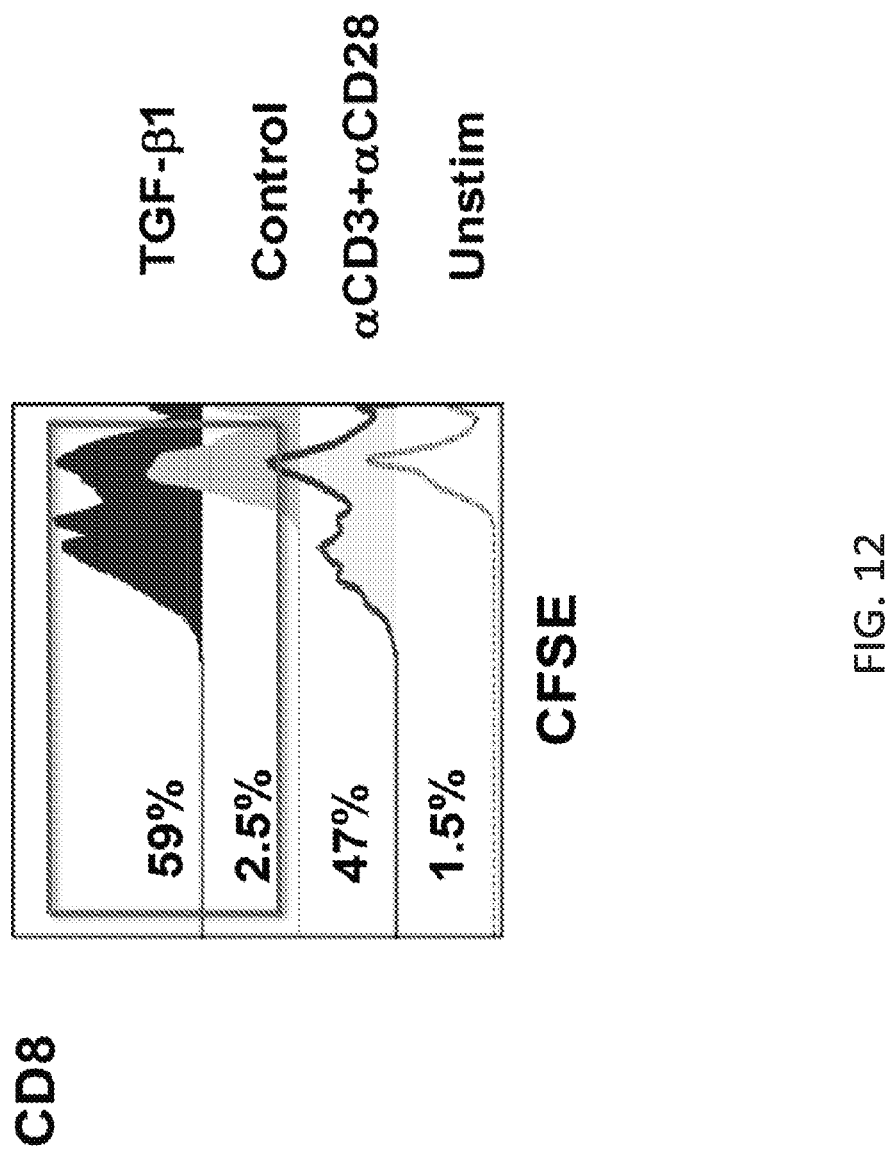
FIG. 12 shows that TGF-β primed MDSC suppress CD8 T cell proliferation less efficiently than control MDSC.

FIG. 11 demonstrates that murine MDSC were produced from bone marrow cells incubated with tumor supernatants in the presence or absence of TGFβ. iNOS expression levels were determined by immunostaining, and NO production by DAF-DA staining followed by flow cytometry TGFβ Alters the Function of Myeloid-Derived Suppressor Cells: Decreased T Cell Suppressive Capacity TGF-β primed MDSC suppress CD8 T cell proliferation less efficiently than control MDSC As shown in FIG. 12, murine MDSC were produced from bone marrow cells incubated with tumor supernatants in the presence or absence of TGFβ. Proliferation of CD8+ T cells in response to CD3/CD28 stimulation in the presence of various ratios of MDSC was determined by CFSE dilution.

Figure 13:
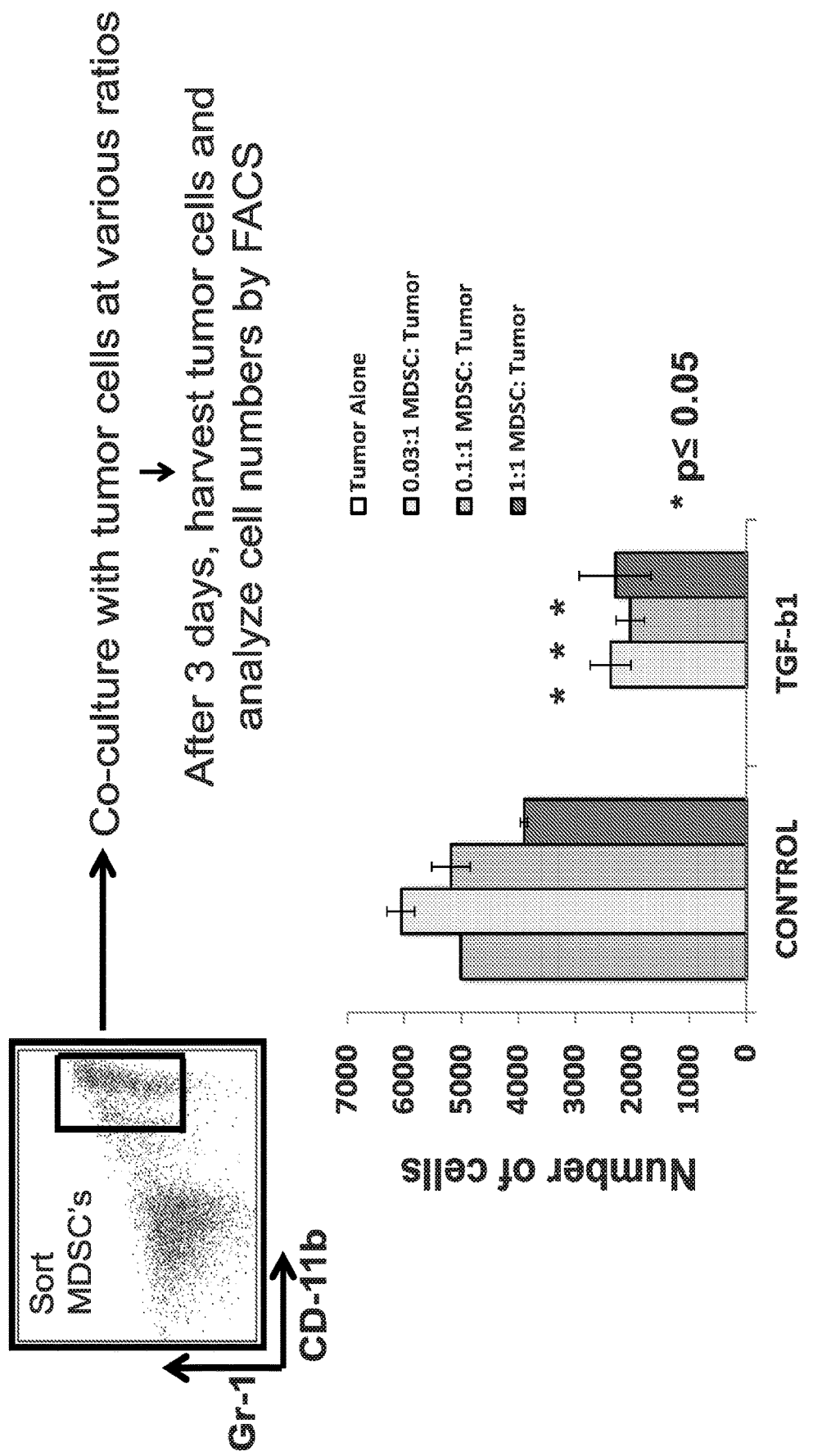
FIG. 13 demonstrates that TGF-β1 primed MDSCs decrease growth of a human oral cancer cell line in in vitro culture.

TGFβ Alters the Function of Myeloid-Derived Suppressor Cells: Acquisition of Tumor Cell Killing Capacity FIG. 13 shows that TGF-β1 primed MDSCs decrease growth of a human oral cancer cell line in in vitro culture.

TGF-β1 primed MDSCs decrease growth of D-hep3 tumors. BM cells were cultured with RET tumor supernatants for four days in the presence or absence of TGF-β1. GR-1 cells were sorted and co-cultured with D-hep3 cells at the following examples of ratios of MDSC:Tumor: 0.03:1; 0.1:1; 0.3:1; 1:1 and 3:1. D-hep3 cells were counted by FACS 48 hrs later.

Figure 14:
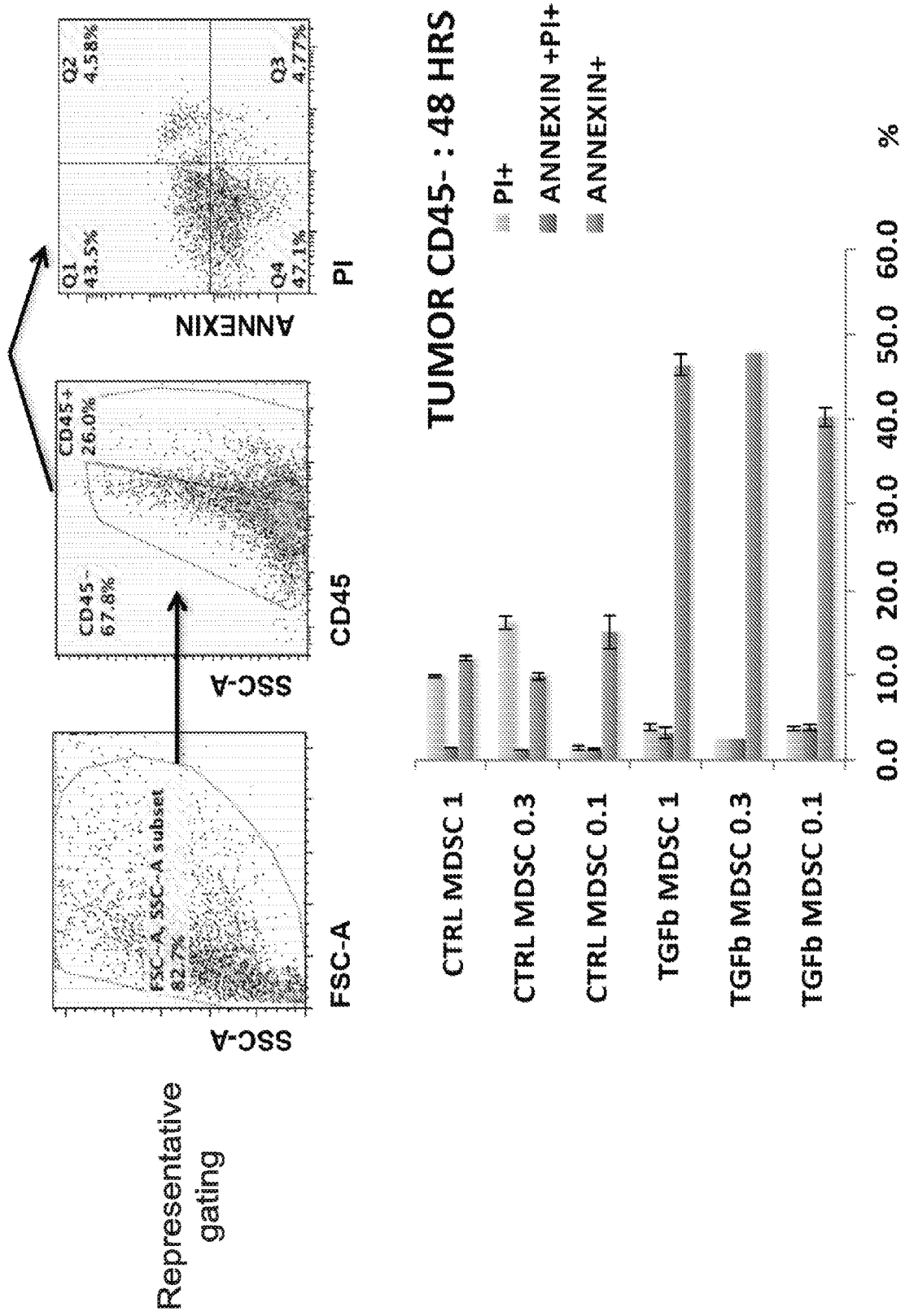
FIG. 14 shows co-culture with TGF-β1 primed MDSCs causes apoptosis of tumor cells in 2D culture.

FIG. 14 demonstrates that co-culture with TGF-β1 primed MDSCs causes apoptosis of tumor cells in 2D culture. Murine bone marrow cells were cultured with tumor supernatants in the presence or absence of TGFβ to produce MDSC. CD11b+ cells were sorted and co cultured with MTEC murine head and neck cancer cells for 48 hours. Cell death and apoptosis were measured using Annexin/PI staining of CD45-negative (tumor) cells.

Figure 15:
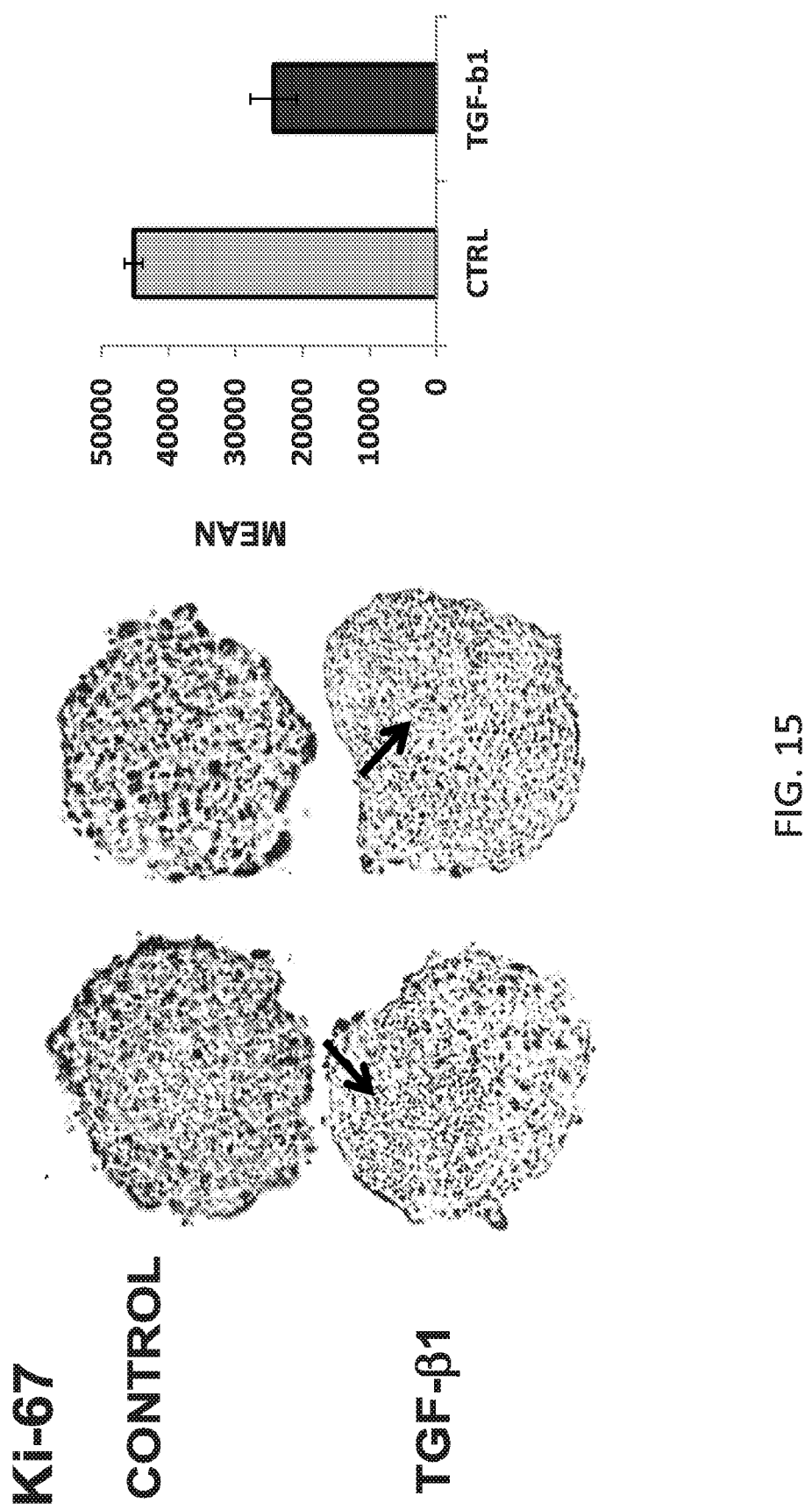
FIG. 15 shows that co-culture with TGF-β1 primed MDSC reduces proliferation of MTEC HNSCC cells grown in 3D spheroid culture.

Co-culture with TGF-β1 primed MDSC reduces proliferation of MTEC HNSCC cells grown in 3D spheroid culture (FIG. 15). Murine bone marrow cells were cultured with tumor supernatants in the presence or absence of TGFβ to produce MDSC. CD11b+ cells were positively selected and co-cultured with MTEC murine HNSCC spheroids for 72 hrs hours before harvest. Spheroids were then embedded and subjected to IHC for the proliferation marker Ki-67.

Figure 16:
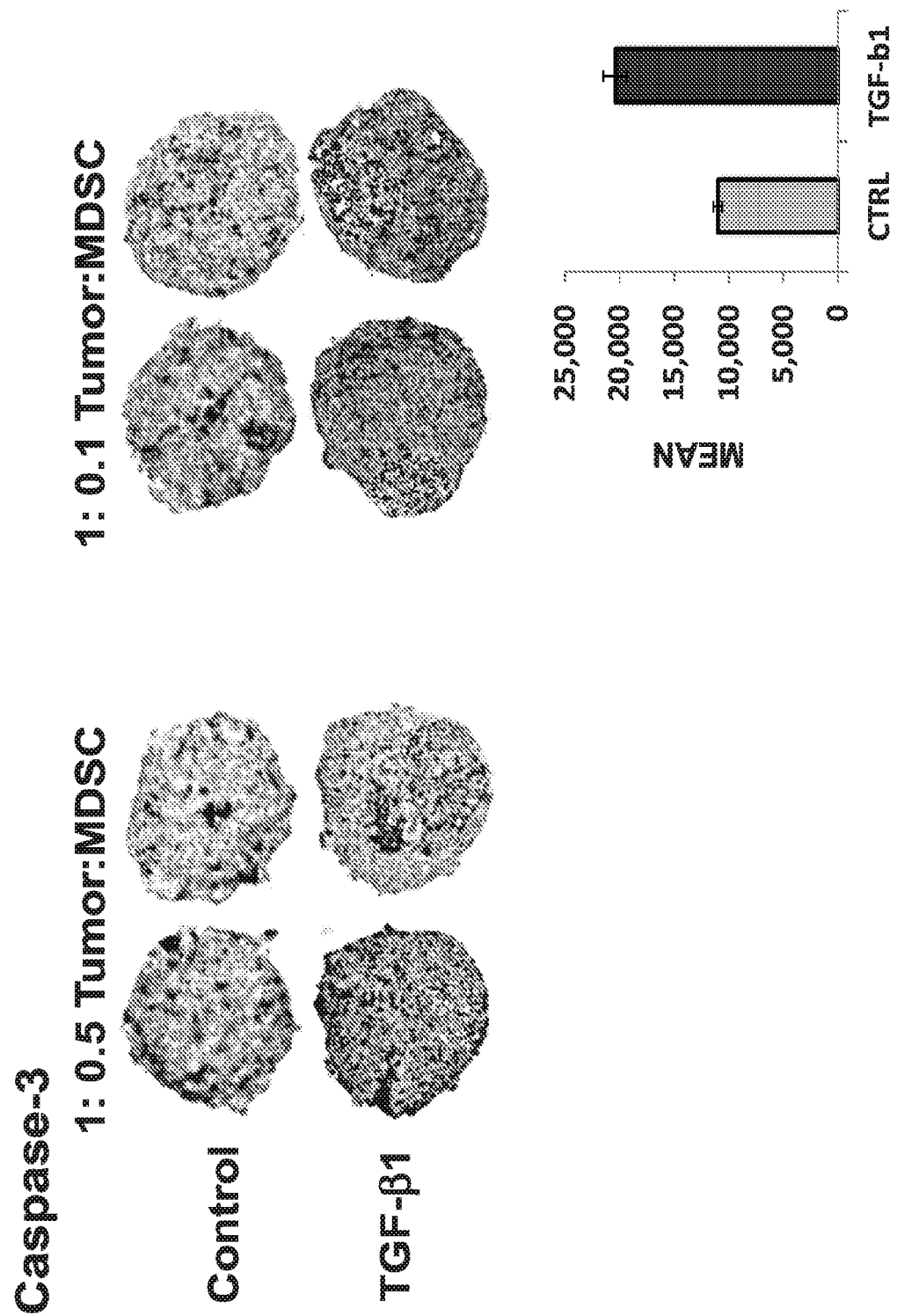
FIG. 16 shows that TGF-β1 primed MDSC enhance apoptosis of MTEC HNSCC cells grown in 3D spheroid culture.

TGF-β1 primed MDSC enhance apoptosis of MTEC HNSCC cells grown in 3D spheroid culture (FIG. 16). Murine bone marrow cells were cultured with tumor supernatants in the presence or absence of TGFβ to produce MDSC. CD11b+cells were sorted and co-cultured with MTEC murine HNSCC spheroids for 72 hours before harvest. Spheroids were then embedded and subjected to IHC for the apoptosis marker caspase-3.

Example 5

Immune Stimulatory Function and Anti-Tumor Activity of TGF-1 Primed Human MDSC

PBMCs were isolated from healthy donor's blood and cultured for 7 days in presence of cytokines (IL-6 and GM-CSF) to generate MDSCs. Different concentrations of TGFβ were added (0, 2.5,5 and 10 ng/ml) during culture. The cells were harvested on day 7, MDSCs (CD33+ cells) were isolated using magnetic beads and cultured with labeled T cells for 4 days to check their suppression function.

Figure 17:
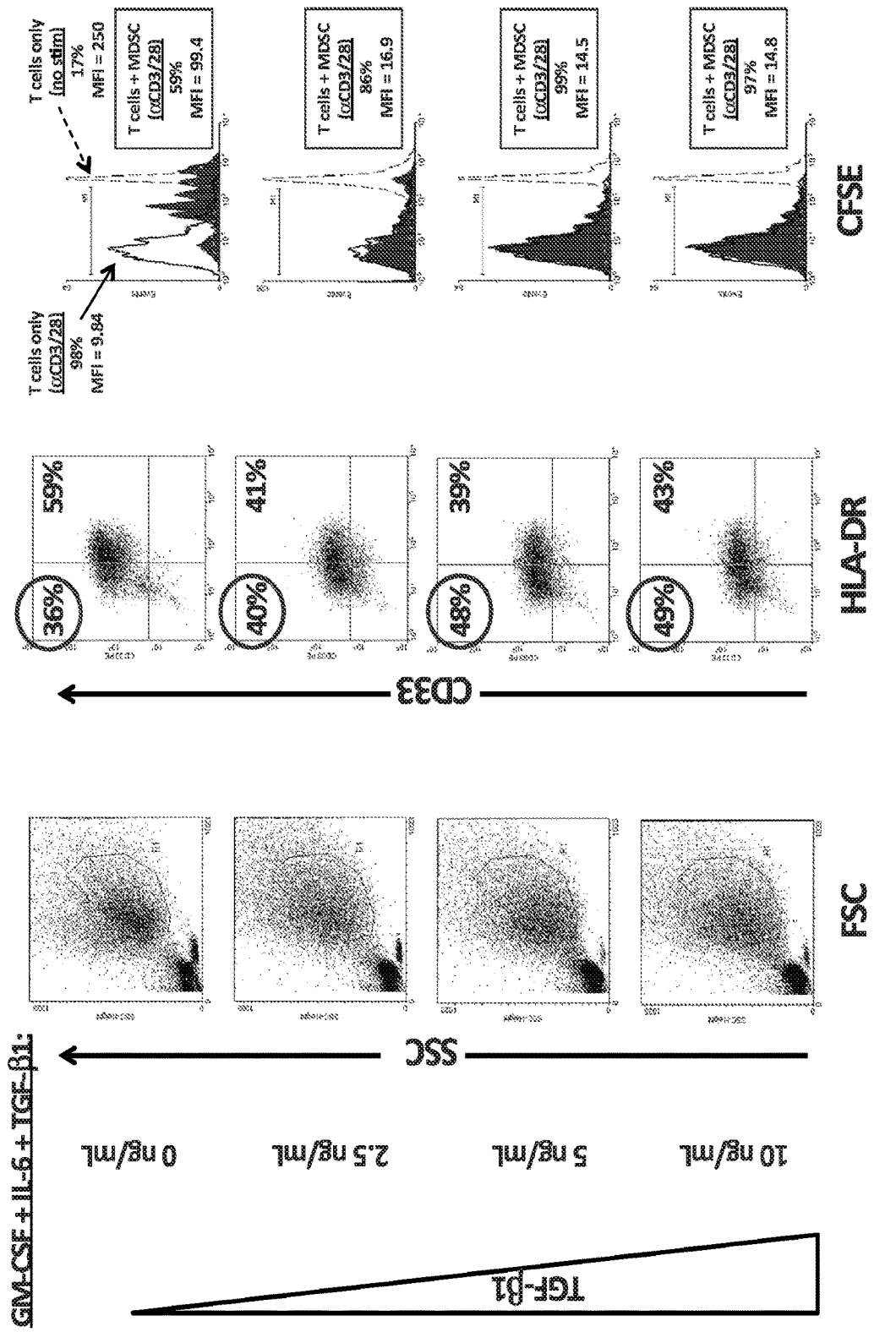
FIG. 17 shows that human TGFβ primed MDSC have decreased capacity to suppress human T cell proliferation.

FIG. 17 shows that TGFβ primed MDSC have decreased capacity to suppress T cell proliferation.

Figure 18:
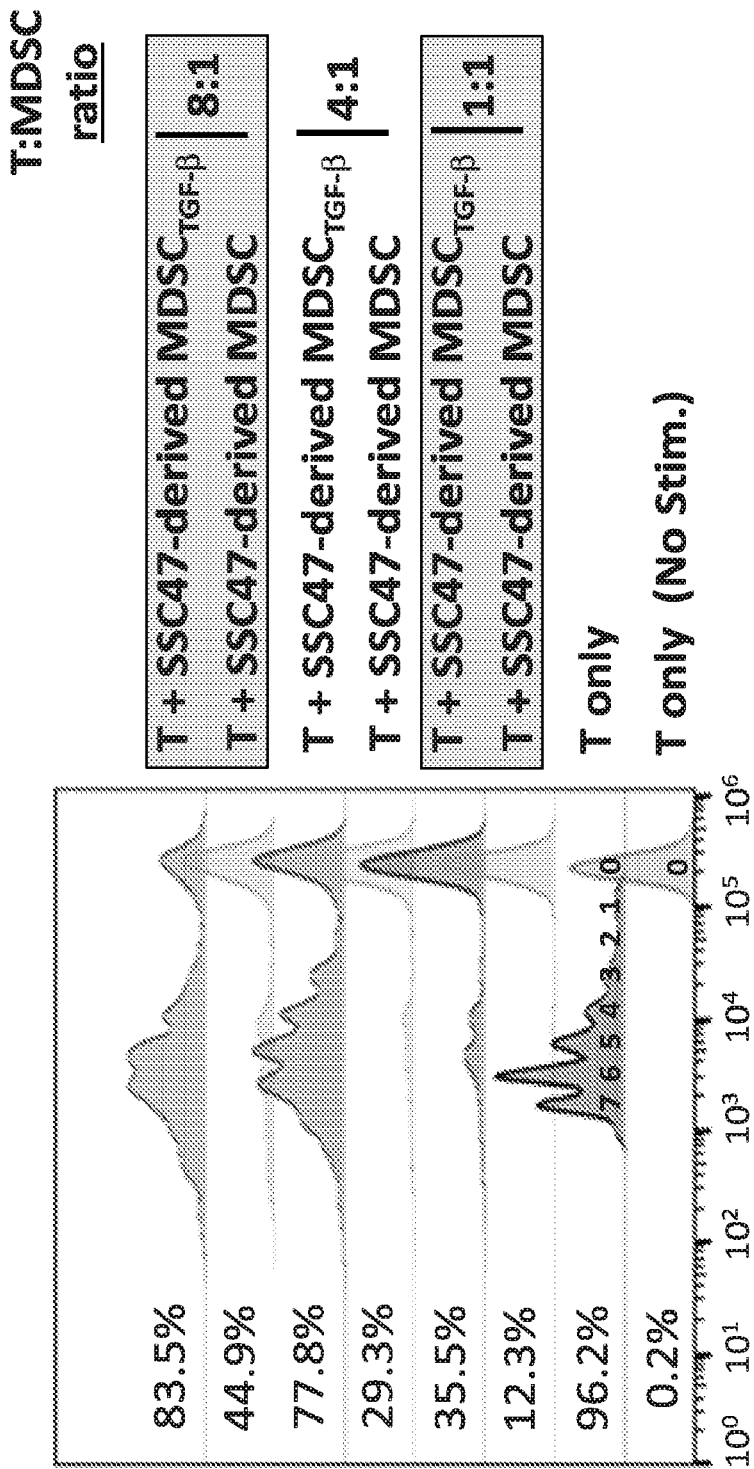
FIG. 18 demonstrates that human TGFβ primed MDSC derived by cytokine co-culture have decreased capacity to suppress human T cell proliferation.

FIG. 18 demonstrates that TGFβ primed MDSC have decreased capacity to suppress T cell proliferation.

Figure 19:
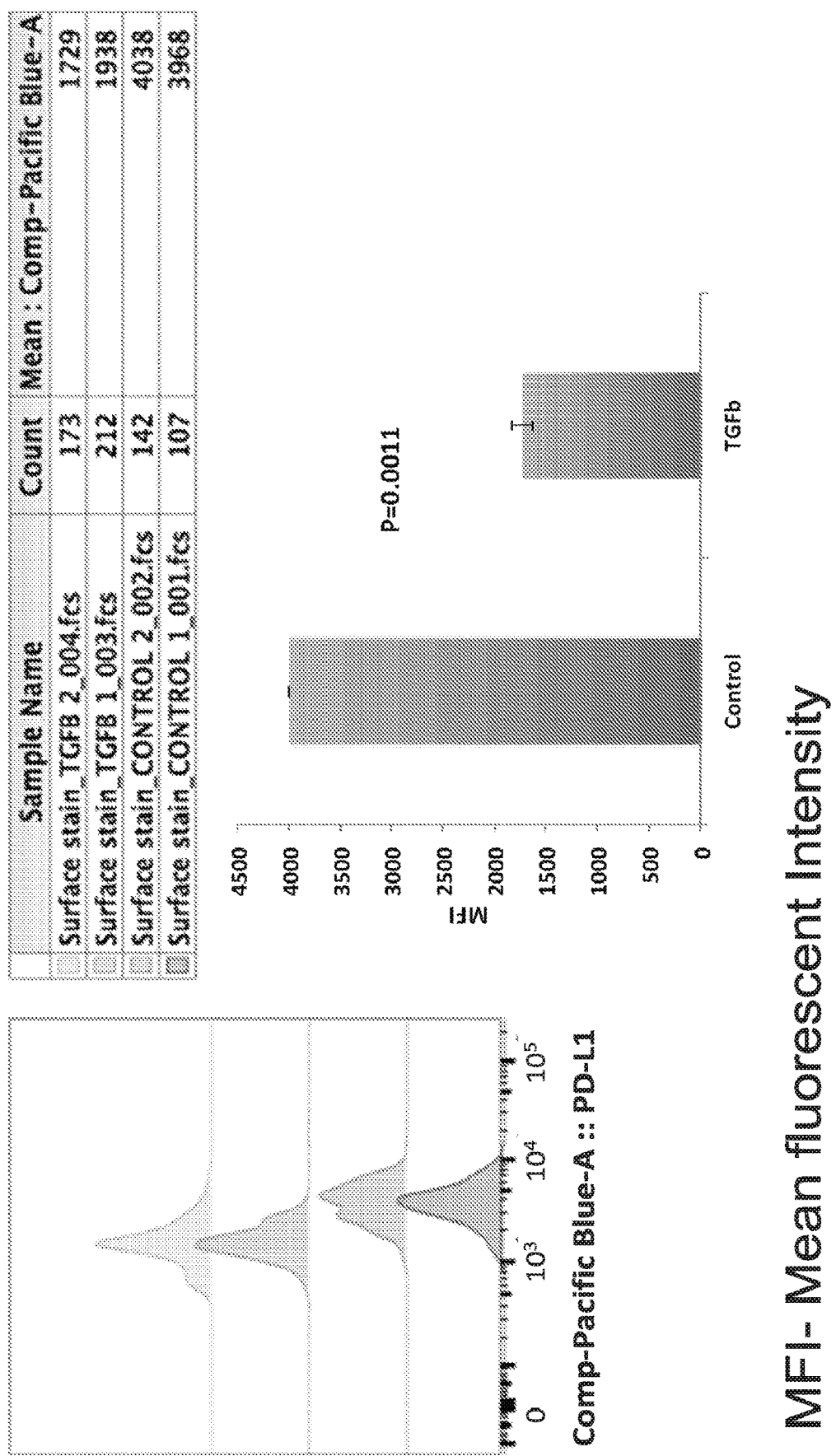
FIG. 19 shows that PD-L1 expression on human MDSC decreases with TGFβ treatment.

Then, PBMCs were cultured for 7 days in presence of SCC47 tumor sup to generate MDSCs in presence or absence of TGFβ as mentioned previously. PDL-1 expression in MDSCs was measured using flow cytometry. PD-L1 expression decreases with TGFβ treatment (FIG. 19).

Figure 20:
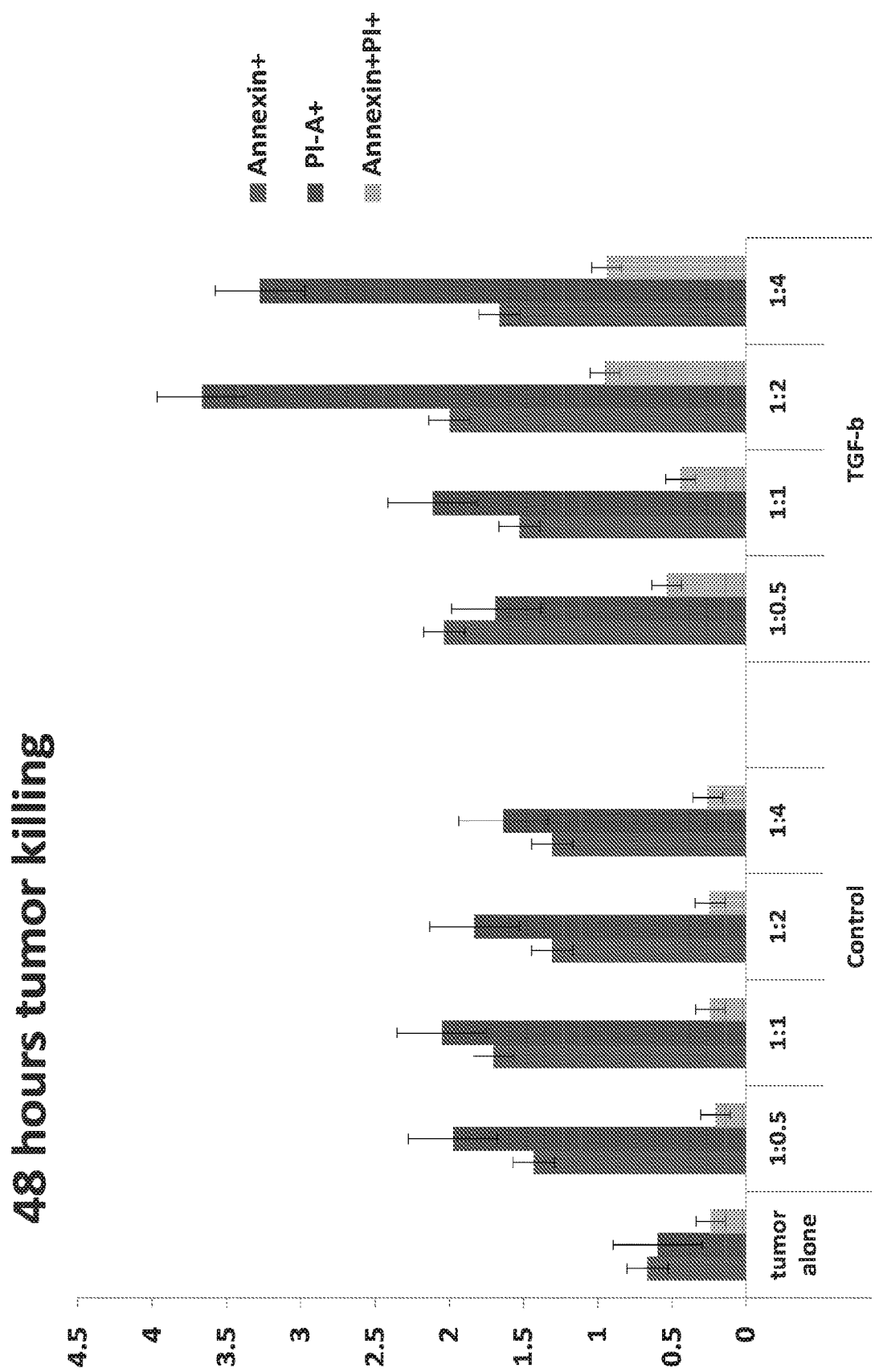
FIG. 20 demonstrates that TGFβ primed human MDSCs have increased ability to kill human head and neck cancer cell line compared to control MDSC.

MDSCs (CD33+ cells) were isolated from PBMC culture using magnetic beads as mentioned earlier. These MDSCs (control and TGFβ primed) were co-cultured with SCC47 tumor cells using different Tumor: MDSC ratios for 48 hours to check their ability to kill tumor cells. As a result, TGFβ primed MDSCs have increased tumor killing (FIG. 20).

Although embodiments of the present invention and its advantages have been described in detail, it should be understood that various changes, substitutions and alterations can be made herein without departing from the spirit and scope of the inventions as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present inventions. Accordingly, the appended claims are intended to include within their scope such processes, machines, manufacture, compositions of matter, means, methods, or steps.

What is claimed is:

1. A method of treating an individual for cancer, comprising the step of providing an effective amount of myeloid-derived suppressor cells (MDSC) comprising anti-tumor activity and/or immune stimulatory activity to the individual, wherein the cells are produced by the following method:
   providing or obtaining bone marrow progenitor cells, peripheral blood mononuclear cells, myeloid-lineage progenitor cells, and/or tumor-resident immature myeloid cells;
   exposing said bone marrow progenitor cells, peripheral blood mononuclear cells, myeloid-lineage progenitor cells, and/or tumor-resident immature myeloid cells to an effective amount of TGF-β1; and
   exposing said bone marrow progenitor cells, peripheral blood mononuclear cells, myeloid-lineage progenitor cells, and/or tumor-resident immature myeloid cells to an effective amount of one or more compositions that induce differentiation of the progenitor cells or tumor-resident immature myeloid cells to MDSCs,
   wherein the steps occur under suitable conditions to produce the plurality of MDSC comprising anti-tumor activity and/or immune stimulatory activity.

2. The method of claim 1, wherein the exposing steps occur ex vivo.

3. The method of claim 1, wherein the exposing steps occur at substantially the same time.

4. The method of claim 1, wherein the exposing steps occur at different times.

5. The method of claim 1, wherein the exposing steps occur at overlapping times.

6. The method of claim 1, wherein the one or more compositions that induce differentiation of the bone marrow progenitor cells, peripheral blood mononuclear cells, myeloid-lineage progenitor cells, and/or tumor-resident immature myeloid cells comprises supernatant from cancer cells.

7. The method of claim 6, wherein the supernatant from cancer cells is obtained from cancer cells engineered to overexpress TGF-β1.

8. The method of claim 1, wherein the one or more compositions that induce differentiation of the bone marrow progenitor cells, peripheral blood mononuclear cells, myeloid-lineage progenitor cells, and/or tumor-resident immature myeloid cells comprises one or more cytokines.

9. The method of claim 8, wherein the cytokines are selected from the group consisting of IL-6, VEGF, IL-1, GM-CSF, M-CSF, TNF-α, Prostaglandin E2, and a combination thereof.

10. The method of claim 8, wherein the cytokines are obtained from the supernatant of cells.

11. The method of claim 1, wherein the effective amount of TGF-β1 is 1 ng/ml through 10 ng/ml.

12. The method of claim 1, wherein the duration of the exposing steps occurs over the course of minutes, hours, days, weeks, or months.

13. The method of claim 12, wherein the duration of the exposing steps occurs over the course of days.

14. The method of claim 13, wherein the duration is from 3-10 days.

15. The method of claim 1, wherein the bone marrow progenitor cells, peripheral blood mononuclear cells, myeloid-lineage progenitor cells, and/or tumor-resident immature myeloid cells are exposed to soluble inflammation-associated signaling mediators.

16. The method of claim 15, wherein the soluble inflammation-associated signaling mediators is selected from the group consisting of PGE2, ATP, adenosine, agonists of toll-like receptors, other receptors driving innate immunity, and a combination thereof.

17. The method of claim 1, wherein the bone marrow progenitor cells, peripheral blood mononuclear cells, myeloid-lineage progenitor cells, and/or tumor-resident immature myeloid cells are obtained from the individual.

18. The method of claim 1, wherein a portion of the plurality of MDSCs are tested for one or more markers.

19. The method of claim 18, wherein the markers are selected from the group consisting of iNOS, NO, ROS, ARG, PD-1, PD-L1, transcription factor CREB, and a cell surface marker.

20. The method of claim 19, wherein the cell surface marker is selected from the group consisting of CD11b, CD33, MHC II, GR-1, and a combination thereof.

21. The method of claim 1, wherein a portion of the plurality of MDSC cells are tested for anti-proliferation activity.

22. The method of claim 1, wherein the individual is provided an additional therapy.

23. The method of claim 22, wherein the additional therapy comprises immunotherapy, chemotherapy, hormone therapy, gene therapy, surgery, radiation therapy, therapy with small molecule inhibitors, or molecular targeted therapy.

* * * * *